United States Patent
Ishikawa et al.

[11] Patent Number: 6,094,265
[45] Date of Patent: Jul. 25, 2000

[54] CALIBRATOR FOR NON-DESTRUCTIVE TRANSMISSION OPTICAL MEASURING APPARATUS

[75] Inventors: Shintaro Ishikawa; Junji Iida; Akira Terashima, all of Chiba, Japan

[73] Assignee: Sumitomo Metal Mining Co., Ltd., Tokyo, Japan

[21] Appl. No.: 09/311,879

[22] Filed: May 14, 1999

[30] Foreign Application Priority Data

May 18, 1998 [JP] Japan .................................. 10-153561
Apr. 15, 1999 [JP] Japan .................................. 11-108475

[51] Int. Cl.$^7$ .................................................. G01N 21/01
[52] U.S. Cl. ...................... 356/244; 356/432; 356/243.1; 209/587
[58] Field of Search ...................... 356/244, 245, 356/246, 243.1, 243.5, 243.8, 432, 433, 434, 440, 442, 436; 250/252.1; 209/564, 580, 587, 588

[56] References Cited

U.S. PATENT DOCUMENTS

| | | | |
|---|---|---|---|
| 5,675,419 | 10/1997 | Van Den Berhg et al. | 356/446 |
| 5,726,750 | 3/1998 | Ito et al. | 356/244 |

FOREIGN PATENT DOCUMENTS

| | | |
|---|---|---|
| 6-258225 | 9/1964 | Japan . |
| 1-284758 | 11/1989 | Japan . |
| 4-115142 | 4/1992 | Japan . |
| 4-116503 | 4/1992 | Japan . |
| 5-142036 | 6/1993 | Japan . |
| 9-15142 | 1/1997 | Japan . |

*Primary Examiner*—Hoa Q. Pham
*Assistant Examiner*—Sang H. Nguyen
*Attorney, Agent, or Firm*—Armstrong, Westerman, Hattori, McLeland, & Naughton

[57] ABSTRACT

In a calibrator used for a non-destructive transmission optical measuring apparatus for quantitatively determining a specific component contained in a measuring object by making light incident on the measuring object at its light-incident area, detecting the light having entered, and having been transmitted through, the interior of the measuring object, at its light-emergent area set at a position different from the light-incident area, and measuring absorption of the light to quantitatively determine the specific component contained in the measuring object, the calibrator comprises a closed body having a light inlet and a light outlet, the interior of which is provided with a substrate having light absorption characteristics identical or similar to those of the specific component, and in which a light path length from the light inlet to the light outlet is so set as to be equal or substantially equal to an effective light path length of the light transmitted through the interior of the measuring object. This calibrator can make calibration on the non-destructive transmission optical measuring apparatus without destroying measuring objects and in a high precision and a good reproducibility and also in a simple way and short time.

8 Claims, 16 Drawing Sheets

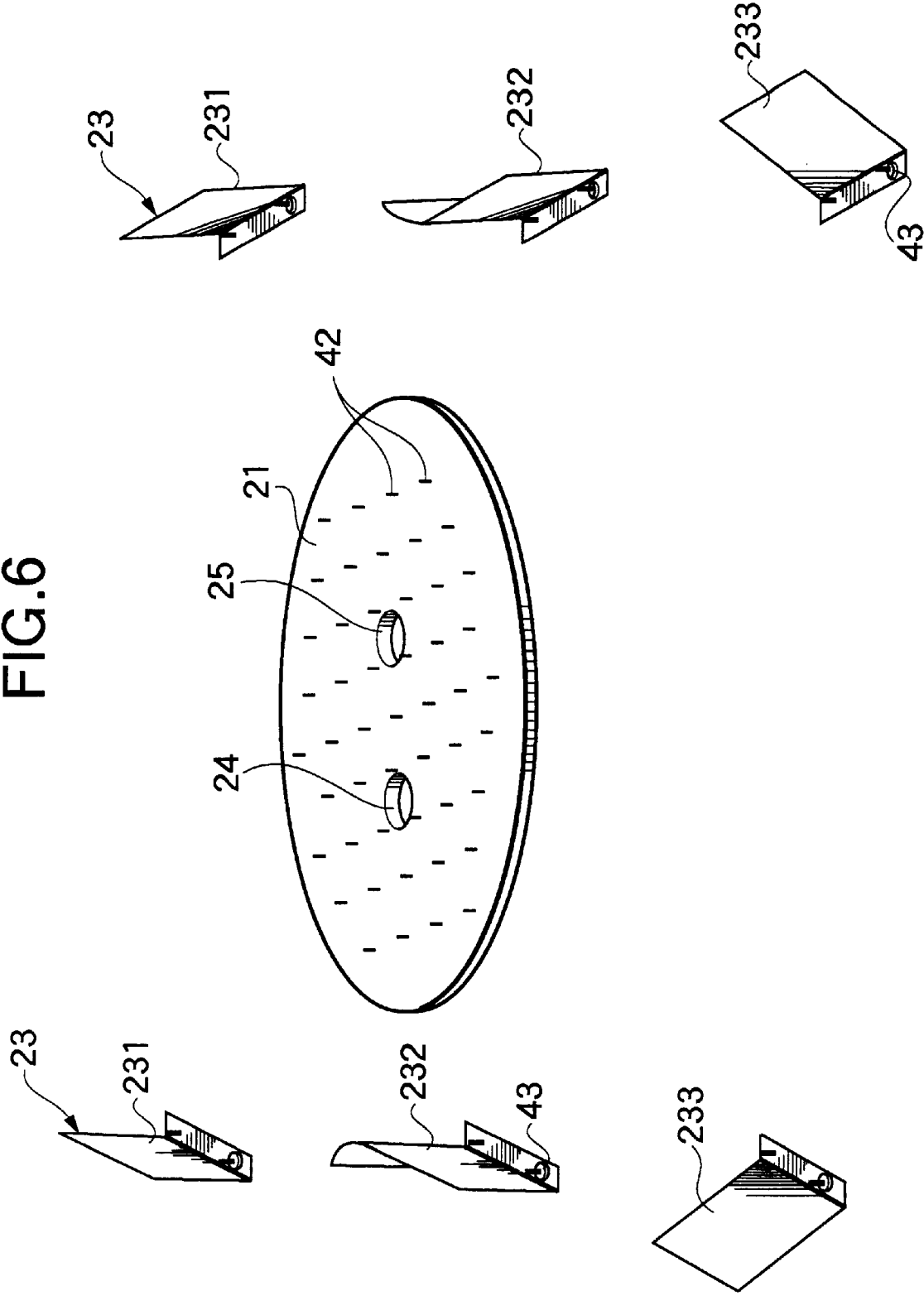

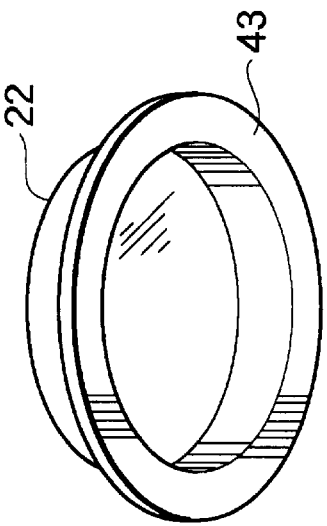
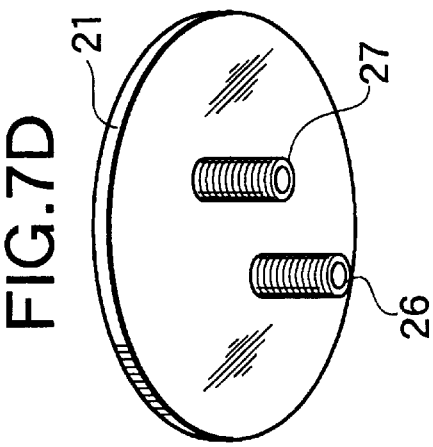
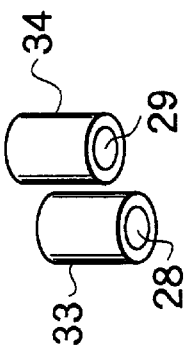
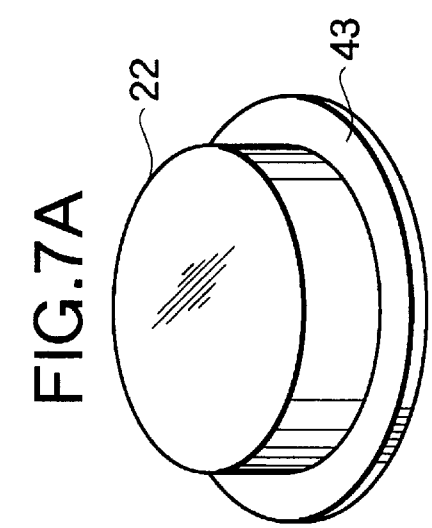
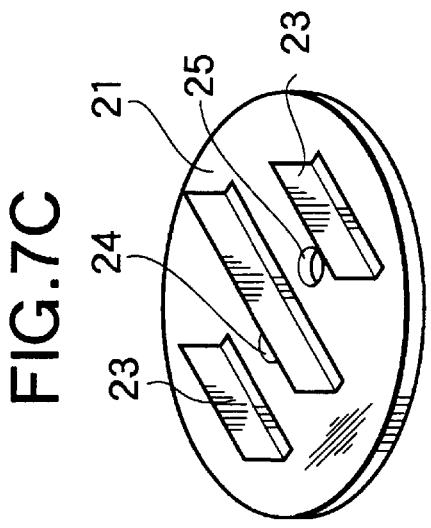

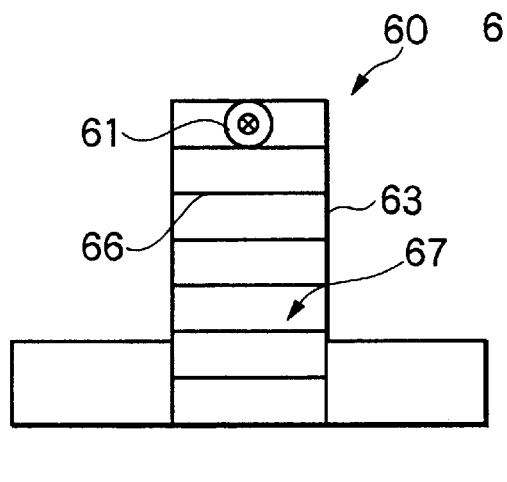
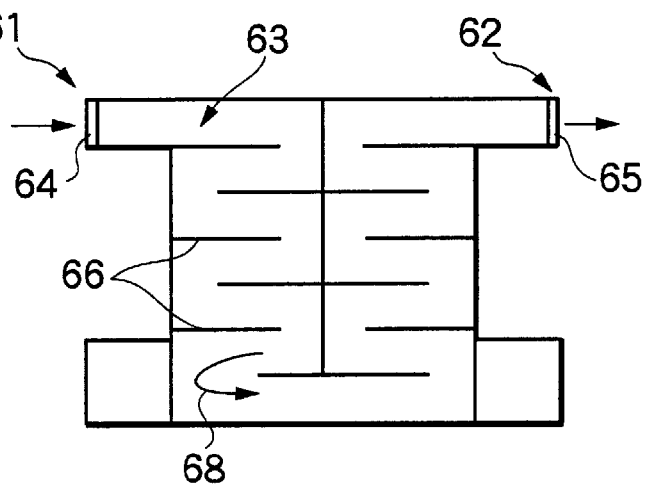
FIG.9A    FIG.9B
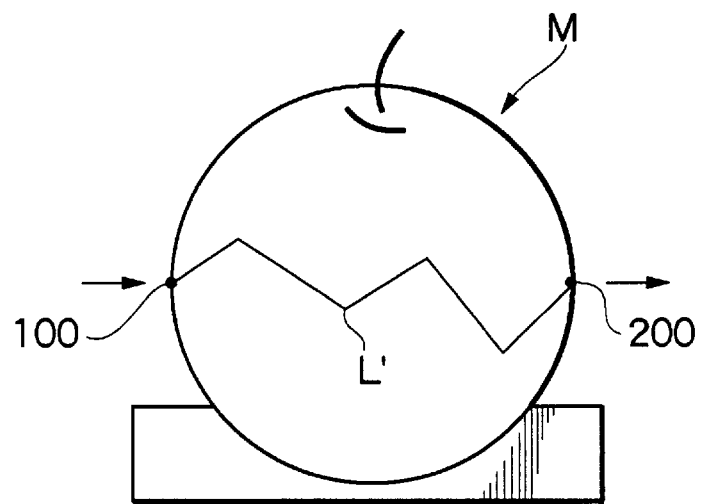
FIG.9C

SUGAR-CONTENT CHANGES CAUSED BY CHANGES
IN THE AMOUNT OF TRANSMITTED LIGHT

SUGAR-CONTENT CHANGES CAUSED BY CHANGES
IN MEASURING LIGHT WAVELENGTH

SUGAR-CONTENT CHANGES CAUSED BY CHANGES IN TEMPERATURE

CALIBRATOR FOR NON-DESTRUCTIVE TRANSMISSION OPTICAL MEASURING APPARATUS

BACKGROUND OF THE INVENTION

1. Field of the Invention

This invention relates to an improvement of a calibrator used for a non-destructive optical measuring apparatus which can quantitatively determine specific components such as sugar contained in measurring objects such as peaches, citrous fruits (or oranges), grapes, tomatoes, muskmelons and watermelons, without destroying the measurring objects. More particularly, it relates to an improvement of a calibrator used for a non-destructive optical measuring apparatus of a light-transmission type.

2. Description of the Related Art

As non-destructive optical measuring apparatus of this type, non-destructive optical measuring apparatus making use of near infrared light are proposed in variety. In order to perform stable and highly precise measurement over a long term by the use of such measuring apparatus, calibrators are indispensable. This is because the long-term service of such non-destructive optical measuring apparatus tends to cause a lowering of measurement precision which is caused by deviations occurring in measuring systems (e.g., deviation of measuring light wavelength used and apparent variation in the amount of incident light and detecting light; the latter being caused by dust or the like having adhered to light-incident and light-emergent portions of the measuring apparatus). Accordingly, various calibrators and calibration methods have been studied and proposed for each of the measuring principle and constitution of non-destructive optical measuring apparatus.

Now, most of non-destructive optical measuring apparatus making use of near infrared light are constituted basically of a white-light source and a spectrometer provided inside the optical measuring apparatus. In such optical measuring apparatus, the light emitted from the white-light source is made incident on a measuring object and the light having reflected from its surface and the vicinity thereof is spectrally analyzed by means of the spectrometer to gain internal information of the measuring object.

In the calibration for non-destructive optical measuring apparatus of such a type, reference samples (references) made of inorganic materials free of changes with time have commonly been used, as exemplified by a glass diffuser panel and a fluorine resin piece. Such reference samples, however, have optical characteristics and temperature characteristics which are different from those of measuring objects in almost all cases, and hence it has been difficult to make highly precise calibration.

Meanwhile, a calibration method is also known in which a sample of the same kind as a measuring object is destructively inspected and the results obtained are compared with the results of non-destructive measurement of the measuring object. However, in an instance where fresh food such as vegetables and fruits are measuring objects, there are problems such that the time during which the sample is available is limited because, e.g., no sample is available in the market even if it is attempted to make calibration for a non-destructive optical measuring apparatus before fruits are actually selected, and not only the destructive measurement, which is manually made, takes a time but also a fairly large number of samples must be put to destructive measurement in order to level scatterings among samples.

Under such technical backgrounds, as disclosed in Japanese Patent Application Laid-open No. 9-15142 a means is proposed as a method of making spectral analysis by using a calibrator having substantially the same optical characteristics as a measuring object and almost not undergoing any changes with time in itself. More specifically, the calibrator (a false fruit) disclosed in this Japanese Patent Application Laid-open No. 9-15142 comprises a calibrator main body of a double-tube structure, which is so constructed that the space between double tubes in this calibrator main body is filled with an aqueous solution containing target components present in the measuring object and also an inner tube of the double tube is made to have a stated light reflectance, or that a suitable dispersoid is added in the filling aqueous solution. At the time of calibration for the non-destructive optical measuring apparatus, in the same way as the measurement on measuring objects, light is made incident on the calibrator from its surface and the light reflecting from the calibrator surface, the filling and the inner tube surface is spectrally analyzed so as to be utilized for the calibration.

Now, the above calibrator (a false fruit) has a structure which accords with the principle of reflection type measurement, and can be effective when used for non-destructive optical measuring apparatus of a reflection type. When, however, used for non-destructive optical measuring apparatus of a transmission type, it has a problem to be solved, as stated later.

More specifically, the non-destructive optical measuring apparatus are known to include reflection type non-destructive optical measuring apparatus in which the cast-back light, having reflected from the surface and the vicinity thereof, is spectrally analyzed to gain internal information of the measuring object as described previously, and transmission type non-destructive optical measuring apparatus in which light is made incident on a measuring object at its light-incident area and the light having entered, and having been transmitted through, the interior of the measuring object is detected at its light-emergent area set at a position different from the light-incident area (i.e., the reflected, cast-back light is not detected and only the transmitted light is detected) to gain the internal information of the measuring object by measuring its light absorption (e.g., absorbance or absorptivity coefficient).

Because of the above difference in type, there is a difference between the reflection type and transmission type non-destructive optical measuring apparatus as stated below. That is, the reflection type non-destructive optical measuring apparatus has had a problem that the light reflecting from the measuring object at its deep part is smaller in amount than the light reflecting from its surface or the vicinity thereof and hence the information of the measuring object at its deep part where the amount of light is relatively small can not successfully be evaluated. Stated specifically, in the case when measuring objects are vegetables and fruits such as muskmelons and watermelons, having thick rind, the information gained in the reflection type is mainly held by that on the rind and is thinly held by that on the sarcocarp. In the case of thin-rind vegetables and fruit, too, it has been difficult to well cope with the matter when it is intended to gain sufficient information on the deep part of the measuring object in respect of its inner-part spoiling, ripeness and so forth.

In contrast thereto, the transmission type non-destructive optical measuring apparatus is of the type that, as described above, the light (transmitted light) having been transmitted through the interior of the measuring object is detected at its position (light-emergent area) different from the light-incident area and the light absorption is measured to gain the internal information of the measuring object, and hence has an advantage that it can be free from the above problem even when the measuring objects are vegetables and fruits having thick rind or when the matter to be measured is the inner-part spoiling and ripeness of measuring objects having thin rind.

In the transmission type non-destructive optical measuring apparatus, however, it is important on account of analysis to know the physical distance at which the transmitted light has passed through the interior of the measuring object (hereinafter "effective light path length"; as distinguished from "light path length", the term "optical path length" used in general definition in physics is meant to be a value obtained when a physical distance at which the light has passed through a medium is multiplied by a refractive index of the medium. In the present specification, the "light path length" is meant to be a physical distance at which the light has traveled through the interior of a measuring object, not multiplied by its refractive index. In the present specification, the term "optical path length" is also used to mean the optical path length as used in the general definition). Accordingly, the light path length of a calibrator used for the transmission type non-destructive optical measuring apparatus has also had to be adjusted to the effective light path length of the measuring object.

More specifically, in the transmission type non-destructive optical measuring apparatus, as shown in FIG. 14, light with a wavelength λ is made incident on a measuring object M such as a muskmelon, and the light having passed through the interior of the measuring object M is detected with a detector S, where specific components such as sugar present in the measuring object are quantitatively determined from, e.g., absorptivity coefficient β (λ) which is found according to the following expression (1):

$$P_{out}(\lambda)=P_{in}(\lambda)\exp[-\beta(\lambda)L] \quad (1)$$

In the expression (1), $P_{in}$ (λ) represents the amount of incident light made incident on the measuring object M, and $P_{out}$ (λ) represents the amount of detecting light, detected with the detector S.

Since, however, the sarcocarp of vegetables and fruits such as muskmelons has light-diffusing properties, as shown in FIG. 14 the light with a wavelength λ, made incident on the measuring object M, does not passes at the shortest distance connecting the light-incident area and light-emergent area on the measuring object M, i.e., at a geometric light path length denoted by L, to go straight toward the detector S, but makes its way to the detector S at last while being scattered at various places inside the measuring object M. Namely, the light having entered the measuring object M travels at a larger light path length (effective light path length L') than the shortest geometric light path length (geometric distance) L. Hence, it follows that the light with a wavelength λ is absorbed in excess by specific components such as sugar in the measuring object M, correspondingly to the longer distance at which the light with a wavelength λ has traveled. More specifically, the absorptivity coefficient β (λ) found by using the geometric light path length (geometric distance L) in the expression (1) is not a true absorptivity coefficient but an apparent absorptivity coefficient, so that its value is larger than the value of a true absorptivity coefficient to tend to be a measured value different from the concentration of a specific component in the measuring object M. For this reason, in the transmission type non-destructive optical measuring apparatus, it is important on account of analysis to know the effective light path length at which the transmitted light has passed through the interior of the measuring object.

Thus, since in the transmission type non-destructive optical measuring apparatus it is important on account of analysis to know the physical distance (effective light path length L') at which the transmitted light has passed through the interior of the measuring object, the light path length of the calibrator used for the transmission type non-destructive optical measuring apparatus has had to be adjusted to the effective light path length of the measuring object. That is, since the deviations occurring in a measuring system are detected as deviations of absorbance and absorptivity coefficient, the calibrator and the measuring object must be made to have equal light path length in order to make equal the amount of deviations of absorbance and absorptivity coefficient which occur in the same measuring system. Namely, this is because the effective light path lengths of the calibrator and measuring object must be adjusted to each other before the calibrator can correct any deviations having occurred in the results of measurement of specific components present in the measuring object.

In the calibrator for the reflection type, disclosed in the above Japanese Patent Application Laid-open No. 9-15142, the effective light path length can not be set at a proper value because of its structure and hence, if used as a calibrator for the transmission type as it is, it has a problem of a difficulty in its practical application.

SUMMARY OF THE INVENTION

The present invention was made taking account of such a problem. Accordingly, an object of the present invention is to provide a calibrator for a non-destructive transmission optical measuring apparatus, the calibrator being able to make calibration on the non-destructive transmission optical measuring apparatus without destroying measuring objects and in a high precision and a good reproducibility and also in a simple way and short time.

Another object of the present invention is to provide a calibrator for a non-destructive transmission optical measuring apparatus, the calibrator being adaptable to a large-sized measuring object and being small-sized and lightweight.

Still another object of the present invention is to provide a calibrator for a non-destructive transmission optical measuring apparatus, the calibrator being adaptable to various measuring objects having different effective light path lengths.

A further object of the present invention is to provide a calibrator for a non-destructive transmission optical measuring apparatus, the calibrator promising a high calibration precision also on non-destructive transmission optical measuring apparatus in which light of plural types having different wavelengths is applied.

The present invention provides a calibrator used for a non-destructive transmission optical measuring apparatus for quantitatively determining a specific component contained in a measuring object by making light incident on the measuring object at its light-incident area, detecting the light having entered, and having been transmitted through, the interior of the measuring object, at its light-emergent area set at a position different from the light-incident area, and measuring absorption of the light to quantitatively determine the specific component contained in the measuring object; the calibrator comprising;

a closed body having a light inlet and a light outlet, the interior of which is provided with a substance having light absorption characteristics identical or similar to those of the specific component, and in which a light path length from the light inlet to the light outlet is so set as to be equal or substantially equal to an effective light path length of the light transmitted through the interior of the measuring object.

BRIEF DESCRIPTION OF THE DRAWINGS

FIG. 6 is a schematic perspective view of a calibrator base disk and partitions which constitute part of the non-destructive transmission optical measuring apparatus calibrator according to the third embodiment.

FIGS. 7A and 7B are a top perspective view and a bottom perspective view, respectively, of a cover which constitutes part of the non-destructive transmission optical measuring apparatus calibrator according to the third embodiment. FIG. 7C is a top perspective view of the calibrator base disk in the course of its assemblage, which constitutes part of the non-destructive transmission optical measuring apparatus calibrator according to the third embodiment, and FIG. 7D is a bottom perspective view thereof. FIG. 7E is a schematic perspective view of first and second outer cylindrical bodies which constitute part of the non-destructive transmission optical measuring apparatus calibrator according to the third embodiment.

FIG. 9A is a sectional front elevation of a non-destructive transmission optical measuring apparatus calibrator according to a fourth embodiment of the present invention, and FIG. 9B is a sectional side elevation thereof. FIG. 9C is a schematic illustration of a non-destructive transmission optical measuring apparatus in which a light-incident area 100 and a light-emergent area 200 with respect to a fruit M are set in the vicinity of the equator of the fruit.

DESCRIPTION OF THE PREFERRED EMBODIMENTS

Figure 1A:
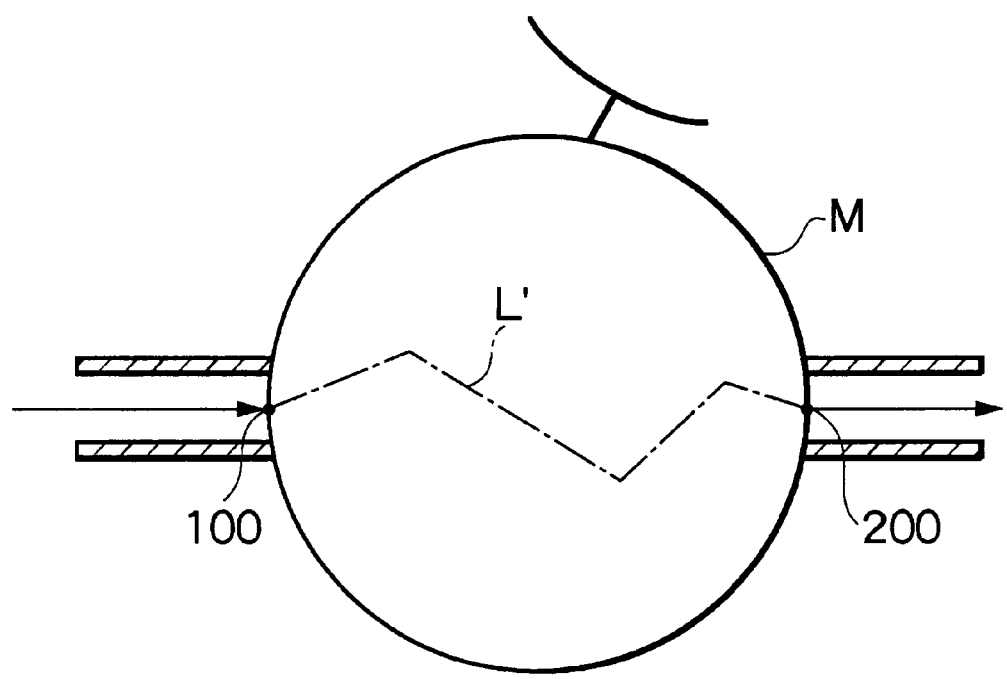
FIG. 1A is a schematic illustration of a non-destructive transmission optical measuring apparatus in which a light-incident area 100 and a light-emergent area 200 with respect to a fruit M are set in the vicinity of the equator of the fruit.

The present invention will be described below in detail.

The present invention is a calibrator used for a non-destructive transmission optical measuring apparatus for quantitatively determining a specific component contained in a measuring object by making light incident on the measuring object at its light-incident area, detecting the light having entered, and having been transmitted through, the interior of the measuring object, at its light-emergent area set at a position different from the light-incident area, and measuring absorption of the light to quantitatively determine the specific component contained in the measuring object. This calibrator is characterized by having a closed body having a light inlet and a light outlet, the interior of which is provided with a substance having light absorption characteristics identical or similar to those of the specific component, and in which a light path length from the light inlet to the light outlet is so set as to be equal or substantially equal to an effective light path length of the light transmitted through the interior of the measuring object.

In the present invention, the closed body has a light inlet and a light outlet and its interior is provided with a substance having light absorption characteristics identical or similar to those of a specific component contained in the measuring object, and the light path length from the light inlet to the light outlet is so set as to be equal or substantially equal to an effective light path length of the light transmitted through the interior of the measuring object. Hence, non-destructive transmission optical measuring apparatus can be calibrated without destroying measuring objects and in a high precision and a good reproducibility and also in a simple way and short time.

The closed body may have a structure wherein its interior is divided by partitions into a plurality of spaces and the spaces form a communicating path connecting the light inlet and the light outlet, thus the light made to enter the closed body from the light inlet is led to the light outlet while repeating its reflection inside the closed body divided by the partitions into a plurality of spaces. Hence, the light path length inside the closed body can be made larger without making the closed body have a larger lengthwise dimension. This can provide a calibrator which is small-sized, lightweight and yet adaptable to large measuring objects such as muskmelons and watermelons.

The number and disposition of the partitions may be set appropriately so that the length of the communicating path can be changed arbitrarily. Accordingly, the partitions may be formed of detachable members so that a calibrator can be provided which is adaptable to various measuring objects having different effective light path lengths.

As the non-destructive transmission optical measuring apparatus for which the calibrator according to the present invention is used, there is an apparatus in which light of plural types having different wavelengths is applied and also an amplifier is incorporated by which signals sent from the detector are converted into voltage. In the non-destructive transmission optical measuring apparatus of this type, a lowering of calibration precision of the calibrator may occur because of a gain variation of the amplifier to signals in an instance where the magnitude of signals obtained when the measuring object is measured is different from the magnitude of signals obtained when the calibrator is measured.

In such a case, an attenuator may be provided so that the magnitude of signals concerning the measuring object can be made equal to the magnitude of signals concerning the calibrator, thus the calibration precision of the calibrator can be prevented from lowering. Especially in the calibrator for the non-destructive transmission optical measuring apparatus in which light of plural types having different wavelengths is applied, the attenuation attributable to the light attenuator may be made equal or substantially equal for each measuring light having different wavelength, thus the calibration precision can be improved.

Embodiments of the present invention will be specifically described below by giving an example of a calibrator for a non-destructive transmission optical measuring apparatus with which, assuming a fruit (a muskmelon or a watermelon) M as a measuring object, the concentration of sugar contained in the fruit M (hereinafter "sugar content") is measured.

First Embodiment

In the non-destructive transmission optical measuring apparatus for which a calibrator 1 according to the present embodiment is used, as shown in FIG. 1A a light-incident area 100 and a light-emergent area 200 with respect to a fruit (muskmelon) M are set in the vicinity of the equator of the fruit.

Figure 1B:
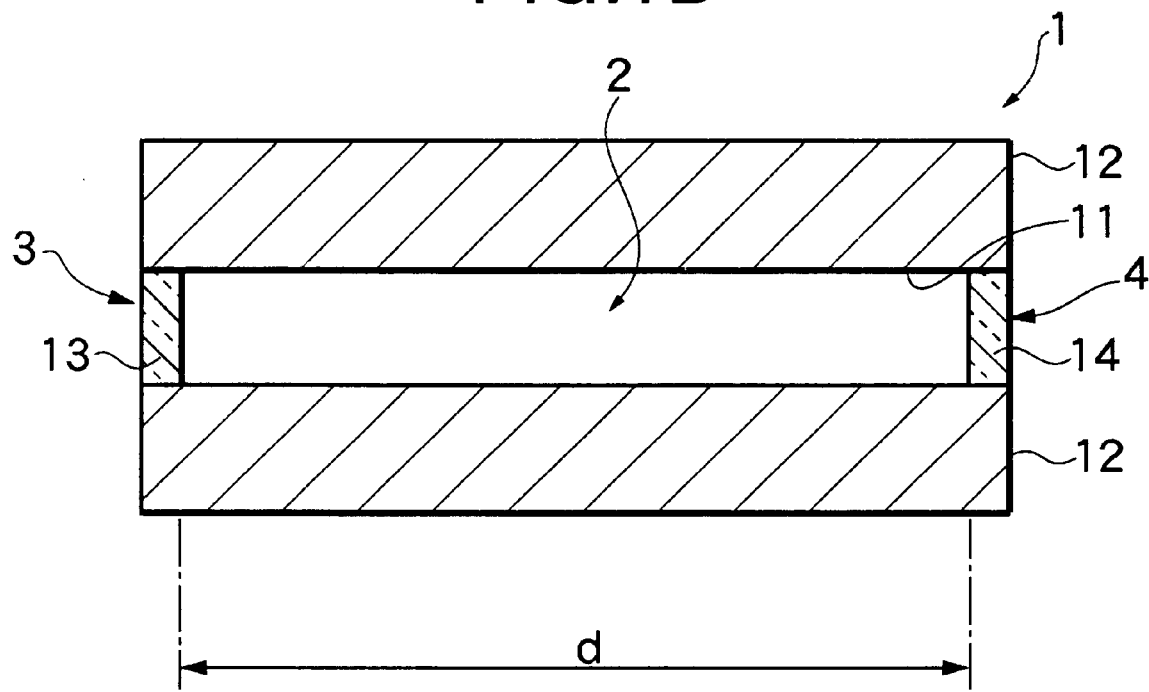
FIG. 1B is a schematic illustration of a calibrator according to a first embodiment of the present invention, used in this non-destructive transmission optical measuring apparatus.

More specifically, as shown in FIG. 1B, the calibrator 1 for a non-destructive transmission optical measuring appa-ratus (i.e., non-destructive transmission optical measuring apparatus calibrator 1) according to the present embodiment is constituted of a linear cylindrical body 11 filled with a cane-sugar solution 2 having a sugar content equal to that of the measuring object, and a calibrator main body 12 formed of black ABS (acrylonitrilebutadiene-styrene) resin, which covers the periphery of the linear cylindrical body 11. The linear cylindrical body 11 is closed with light-transmitting members 13 and 14 at its both open ends. Also, the end closed with the light-transmitting member 13 constitutes a light inlet 3, and the end closed with the light-transmitting member 14 constitutes a light outlet 4. The light path length measured from the light inlet 3 to the light outlet 4 (i.e., the light path length of the interior of the linear cylindrical body 11 filled with the cane sugar solution 2) is so set as to be substantially equal to the effective light path length L' of the light transmitted through the interior of the fruit M.

Here, the reason why the light path length measured from the light inlet 3 to the light outlet 4 (i.e., the light path length of the interior of the linear cylindrical body 11 filled with the cane sugar solution 2) of the non-destructive transmission optical measuring apparatus calibrator 1 is adjusted to the effective light path length L' is, as stated previously, to accurately correct variations in sugar content which are caused by deviations having occurred in the measuring system. The "deviations" in the measuring system refer to, e.g., deviation of measuring light wavelength and apparent variation in the amount of transmitted light; the latter being caused by dust or the like having adhered to light-incident and light-emergent portions of the non-destructive transmission optical measuring apparatus. Since such deviations occurring in the measuring system are detected as deviations of absorbance and absorptivity coefficient, the calibrator and the measuring object must be made to have equal light path length in order to make equal the amount of deviations of absorbance and absorptivity coefficient which occur in the same measuring system between the calibrator and the measuring object. Namely, this is because their effective light path lengths must be adjusted to each other before the calibrator can accurately correct any changes in sugar content which have occurred in the measuring object because of the deviations in the measuring system.

Figure 15:
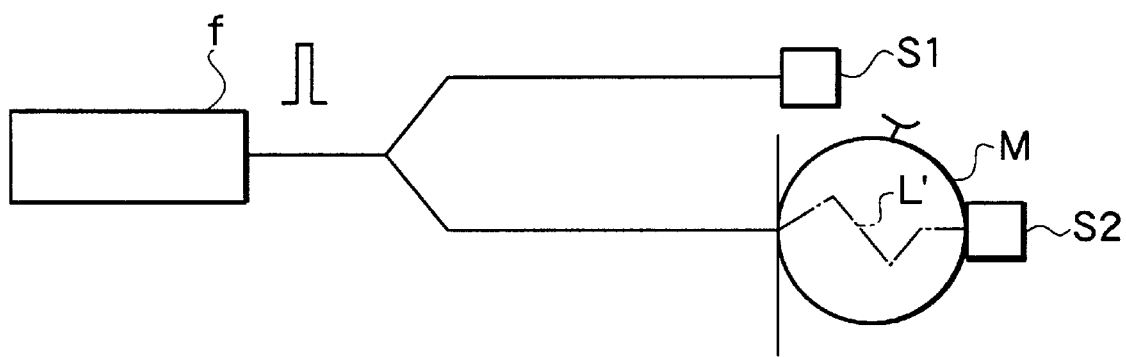
FIG. 15 illustrates an example of a measuring method for determining effective light path length L'.

The effective light path length L' of the measuring object may be determined by, e.g., as shown in FIG. 15, using one pulse laser light source f and two detectors, first and second detectors S1 and S2.

More specifically, the distance from the pulse laser light source f to the first detector S1 is set equal to the distance from the pulse laser light source f to the light-incident area on the measuring object (fruit) M, and the pulse laser light emitted from the pulse laser light source f is branched at the middle of the light path. Also, the pulse laser light is made to enter the one first detector S1 directly and the pulse laser light transmitted through the interior of the measuring object (fruit) M is made to enter the other second detector S2 disposed on the measuring object (fruit) M in close contact with its light-emergent area. Then, the time difference $\Delta t$ between pulses reaching the first and second detectors S1 and S2 is multiplied by light velocity C ($C \times \Delta t$), thus a value (L'$\times$n') can be determined which is obtained when the effective light path length L' in the measuring object (fruit) M is multiplied by refractive index n' of the sarcocarp in the fruit M.

Figure 16:
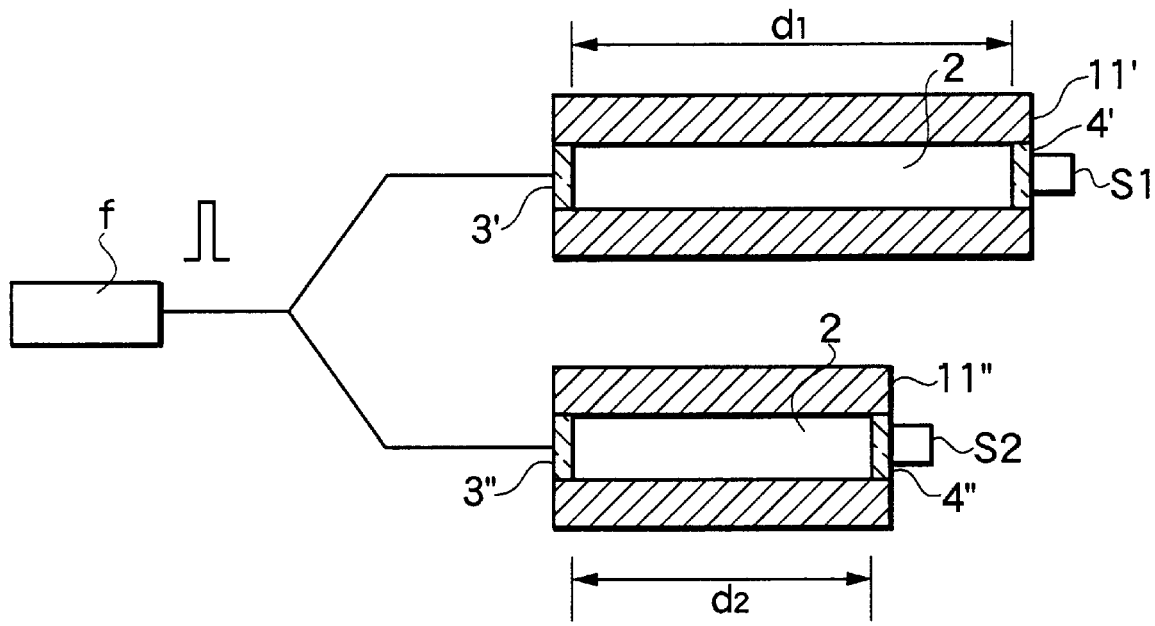
FIG. 16 illustrates an example of a measuring method for determining light path length ΔL" per geometrical unit length of the interior of a linear cylindrical body filled with a cane sugar solution.

Geometrical length d of the linear cylindrical body 11, necessary for setting the light path length from the light inlet 3 to the light outlet 4 (i.e., the light path length of the interior of the linear cylindrical body 11 filled with the cane sugar solution 2) substantially equal to the effective light path length L' in the measuring object (fruit) M may also be determined by, as shown in FIG. 16, using one pulse laser light source f and two detectors, first and second detectors S1 and S2.

More specifically, a pair of linear cylindrical bodies 11' and 11" are prepared which are fitted with diffusion type attenuation plates, described later, at its ends closed with the light-transmitting members, have geometrical lengths d1 and d2, respectively, and are each filled with a cane sugar solution 2. The distance from the pulse laser light source f to a light inlet 3' of the linear cylindrical body 11' is set equal to the distance from the pulse laser light source f to a light inlet 3" of the linear cylindrical body 11", and a first detector SI and a second detector S2 are disposed on the linear cylindrical bodies 11' and 11" in close contact with their light outlets 4' and 4", respectively. Then, the pulse laser light emitted from the pulse laser light source f is branched at the middle of the light path. The one pulse laser light is made to be transmitted through the linear cylindrical body 11' and enter the first detector S1 directly and the other pulse laser light is made to be transmitted through the linear cylindrical body 11" and enter the second detector S2.

Where the time for which a pulse has reached the first detector S1 is represented by t1 and the time for which a pulse has reached the second detector S2 by t2, a measured optical path length $\alpha 1$ of the linear cylindrical body 11' [i.e., optical path length obtained by adding i) a portion of optical path length given by the thickness of the two light-transmitting members and the thickness of the diffusion type attenuation plates, described later, attached to these to ii) the optical path length of the interior of the linear cylindrical body 11' filled with the cane sugar solution 2] corresponds to a value obtained by (light velocity C×t1), and also a measured optical path length $\alpha 2$ of the linear cylindrical body 11" [i.e., optical path length obtained by adding i) a portion of optical path length given by the thickness of the two light-transmitting members and the thickness of the diffusion type attenuation plates, described later, attached to these to ii) the optical path length of the interior of the linear cylindrical body 11" filled with the cane sugar solution 2] corresponds to a value obtained by (light velocity C×t2).

Hence, light path length $\Delta L''$ per geometrical unit length of the interior of the linear cylindrical body filled with a cane sugar solution 2 having refractive index n" can be determined by:

$$n'' \times \Delta L'' = (\alpha 1 - \alpha 2)/(d1 - d2)$$

That is, although the portion of optical path length given by the thickness of the two light-transmitting members and the thickness of the diffusion type attenuation plates attached to these has been added in the measured optical path length $\alpha 1$ of the linear cylindrical body 11' and measured optical path length $\alpha 2$ of the linear cylindrical body 11", the optical path length thus added is cancelled by subtracting the measured optical path length $\alpha 2$ from the measured optical path length $\alpha 1$, thus a value can be determined which is obtained when the light path length $\Delta L''$ per geometrical unit length of the interior of the linear cylindrical body filled with the cane sugar solution 2 is multiplied by refractive index n" of the cane sugar solution.

Therefore, the geometrical length d of the linear cylindrical body 11, necessary for setting the light path length of the interior of the linear cylindrical body 11 filled with the cane sugar solution 2 substantially equal to the effective light path length L' in the measuring object (fruit) M can be determined by:

$$d = (L' \times n')/(\Delta L'' \times n'') = L'/\Delta L''$$

(but on condition that the refractive index n' of the sarcocarp in the fruit M is substantially equal to the refractive index n" in the cane sugar solution).

On the inner wall surface of the linear cylindrical body 11 from which surface the light having entered the calibrator 1 reflects, a gold-plated light-reflecting film (not shown) is provided which has little dependence of reflectance on wavelength within the range of measuring light wavelengths and also has a good corrosion resistance.

In this non-destructive transmission optical measuring apparatus, an amplifier is also incorporated by which signals sent from the detector are converted into voltage. Then, as a variation factor of measurement results, a gain variation of this amplifier is also possible. Stated specifically, in an instance where the magnitude of signals concerning the measuring object is different from the magnitude of signals obtained when the calibrator is measured, there is a possibility that actual variations can not be accurately measured because of a difference in the gain for each signal of the amplifier. Accordingly, an attenuator may preferably be added so that the amount of transmitted light of the calibrator can be made substantially equal to that of the measuring object. Such an attenuator may also preferably have an equal attenuation for each measuring light having different wavelength within the range of measuring light wavelengths. This is because any great variation of the attenuation within the range of measuring light wavelengths makes the behavior of transmitted light different between the calibrator and the measuring object upon deviation of measuring light wavelength to make accurate calibration impossible. The attenuator is exemplified by an aperture type attenuator, a surface scattering type attenuator and a diffusion type attenuator, any of which may be used alone or in combination of two or more.

In the non-destructive transmission optical measuring apparatus calibrator according to the present embodiment as shown in FIG. 1B, the amount of transmitted light is larger than that of the measuring object. Accordingly, the light-transmitting members 13 and 14 on the both ends of the linear cylindrical body 11 are each fitted with a ready-made diffusion type attenuation plate and a ready-made aperture type attenuator in combination, the former having an equal attenuation for each measuring light having different wavelength. The amount of transmitted light is roughly adjusted by the diffusion type attenuation plate and also micro-adjusted by controlling the window diameter of the aperture type attenuator. Using these two types of attenuators, the amount of transmitted light of the calibrator is made equal to that of the measuring object.

The non-destructive transmission optical measuring apparatus calibrator according to the first embodiment constituted as described above is put in the preset measuring position in the non-destructive transmission optical measuring apparatus. Then, the light having entered the linear cylindrical body 11 from the light inlet 3 passes through the interior of the filled cane sugar solution 2 while repeating its reflection inside the linear cylindrical body 11, and enters a detector (not shown) of the non-destructive transmission optical measuring apparatus from the light outlet 4. Thus, the sugar content of the cane sugar solution 2 with which the interior of the calibrator is filled can be determined like the fruit sugar content on the basis of the amount of light measured by the detector.

The difference in sugar content between the sugar content thus determined at the time of calibration and the reference sugar content of the cane sugar solution 2 in the calibrator which is previously measured under certain conditions is modulated by correcting it on a software of the non-destructive transmission optical measuring apparatus, thus the operation of calibration is completed.

The fruit sugar content measured after the calibration can be an accurate sugar content from which any sugar content variations caused by the deviation in the measuring system in the non-destructive transmission optical measuring apparatus have been removed.

Here, in the non-destructive transmission optical measuring apparatus calibrator 1 according to the present embodiment, the interior of the linear cylindrical body (closed body) 11 is filled with the cane sugar solution 2 having a sugar content equal to that of the specific component contained in the measuring object. In addition to this cane sugar solution 2, a light-scattering material such as cellulose fiber may be mixed. This can make greater the scattering of light entering the linear cylindrical body 11. Thus, compared with the instance where the light-scattering material is not added, the light having entered the linear cylindrical body 11 travels in excess because of the greater scattering of light, through the interior of the linear cylindrical body 11 filled with the cane sugar solution 2, and hence the geometrical lengthwise dimension of the linear cylindrical body (closed body) 11 can be set shorter correspondingly, bringing about an advantage that the calibrator can be made small-sized.

Second Embodiment

Figure 2A:
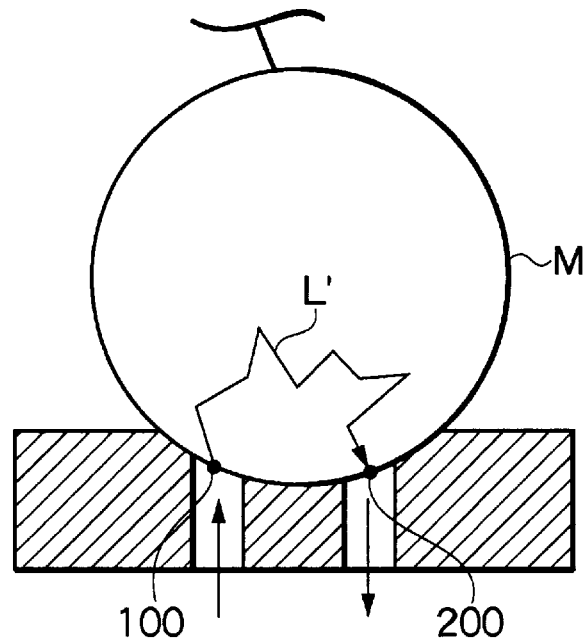
FIG. 2A is a schematic illustration of a non-destructive transmission optical measuring apparatus in which a light-incident area 100 and a light-emergent area 200 with respect to a fruit M are set in the vicinity of the bottom of the fruit.
Figure 2B:
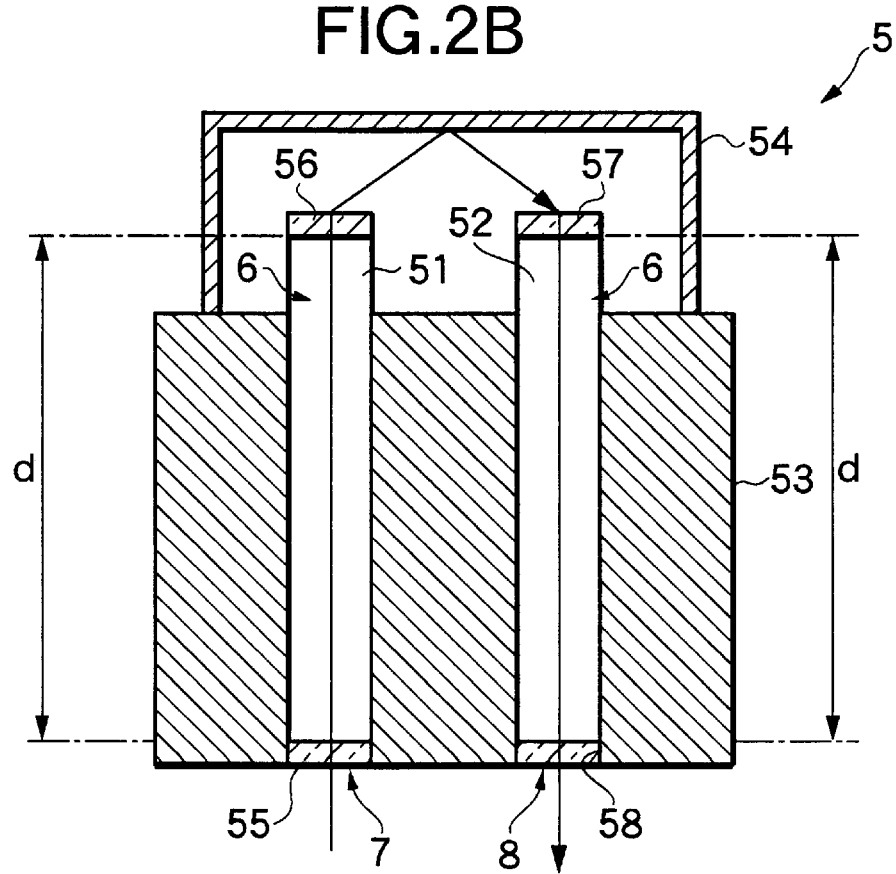
FIG. 2B is a schematic illustration of a calibrator according to a second embodiment of the present invention, used in this non-destructive transmission optical measuring apparatus.

FIGS. 2A and 2B shows a second embodiment of the present invention. The calibrator according to the present embodiment is a calibrator used for a non-destructive transmission optical measuring apparatus in which, as shown in FIG. 2A, a light-incident area 100 and a light-emergent area 200 with respect to a fruit (muskmelon) M are positioned in the vicinity of the bottom of the fruit M.

More specifically, as shown in FIG. 2B, a non-destructive transmission optical measuring apparatus calibrator 5 according to the present embodiment is constituted of i) a pair of linear cylindrical bodies 51 and 52 which are filled with a cane sugar solution 6 having a sugar content equal to that of the measuring object (fruit M), are provided in parallel to each other and are set to have geometrical lengths d equal to each other, ii) a calibrator main body 53 formed of black ABS (acrylonitrile-butadiene-styrene) resin, which covers the peripheries of the pair of linear cylindrical bodies 51 and 52, iii) and a cover member 54 made of stainless steel, which is so provided as to cover one ends of the linear cylindrical bodies 51 an 52 and by which the light emergent from an end of the one linear cylindrical body 51 is made incident on an end of the other linear cylindrical body 52. These linear cylindrical bodies 51 and 52 are closed with light-transmitting members 55, 56 and 57, 58, respectively, at their both open ends. Also, the end closed with the light-transmitting member 55 constitutes a light inlet 7, and the end closed with the light-transmitting member 58 constitutes a light outlet 8.

The light path length in total, of the interiors of the pair of linear cylindrical bodies 51 and 52 filled with the cane sugar solution 6 (the light path length at which the light travels through the interior of the cane sugar solution 6) is so set as to be substantially equal to the effective light path length L' of the light transmitted through the interior of the fruit M.

Here, the reason why the total light path length of the interiors of the pair of linear cylindrical bodies 51 and 52 filled with the cane sugar solution 6 is adjusted to the effective light path length L' is the same as that in the calibrator 1 according to the first embodiment shown in FIG. 1.

Figure 17:
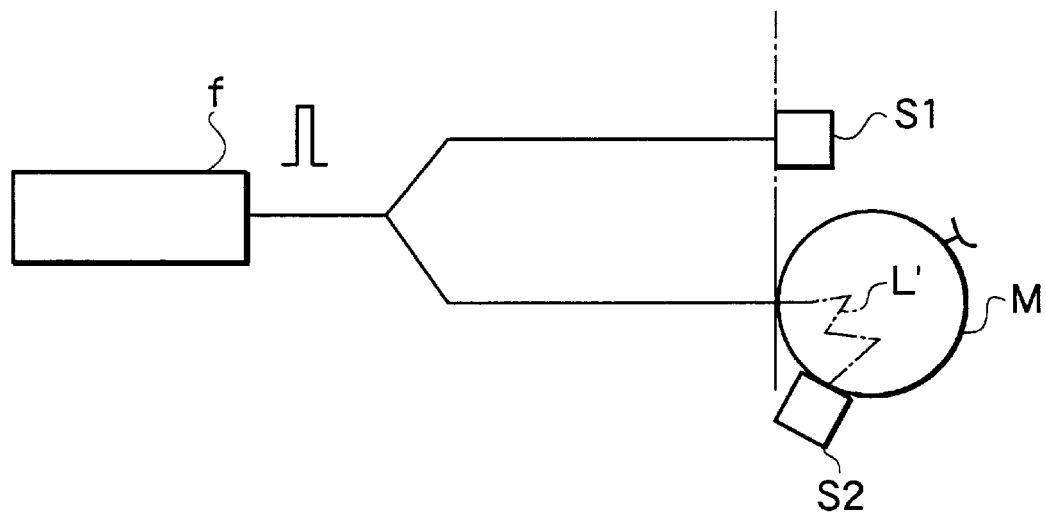
FIG. 17 illustrates another example of a measuring method for determining effective light path length L'.

The effective light path length L' of the measuring object fruit M may be determined by, e.g., as shown in FIG. 17, using one pulse laser light source f and two detectors, first and second detectors S1 and S2. More specifically, the distance from the pulse laser light source f to the first detector S1 is set equal to the distance from the pulse laser light source f to the light-incident area on the measuring object (fruit) M, and the pulse laser light emitted from the pulse laser light source f is branched at the middle of the light path. Also, the pulse laser light is made to enter the one first detector S1 directly and the pulse laser light transmitted through the interior of the measuring object (fruit) M is made to enter the other second detector S2 disposed on the measuring object (fruit) M in close contact with its light-emergent area. Then, the time difference $\Delta t$ between pulses reaching the first and second detectors S1 and S2 is multiplied by light velocity C (C×$\Delta t$), thus a value (L'×n') can be determined which is obtained when the effective light path length L' in the measuring object (fruit) M is multiplied by refractive index n' of the sarcocarp in the fruit M.

Geometrical lengths d of the linear cylindrical bodies 51 and 52, necessary for setting the total light path length of the interiors of the pair of linear cylindrical bodies 51 and 52 filled with a cane sugar solution 6 having refractive index n" (the light path length at which the light travels through the interior of the cane sugar solution 6) substantially equal to the effective light path length L' in the fruit M may also be determined by the same method as described in the first embodiment. More specifically, using one pulse laser light source f and two detectors, first and second detectors S1 and S2 as shown in FIG. 16, a pair of linear cylindrical bodies 11' and 11" may be incorporated which are fitted with diffusion type attenuation plates at its ends closed with the light-transmitting members, have geometrical lengths d1 and d2, respectively, and are each filled with a cane sugar solution 2, where the light path length $\Delta L$" per geometrical unit length of the interior of the linear cylindrical body may be determined by:

$$n" \times \Delta L" = (\alpha 1 - \alpha 2)/(d1 - d2).$$

On the basis of this $\Delta L$", the pair of linear cylindrical bodies 51 and 52 may be so disposed that their total light path length may become substantially equal to the effective light path length L' in the measuring object (fruit) M.

That is, the geometrical lengths d of the linear cylindrical bodies 51 and 52 can be determined by:

$$2d = (L' \times n')/(\Delta L" \times n") = L'/\Delta L"$$

(but on condition that the refractive index n' of the sarcocarp in the fruit M is substantially equal to the refractive index n" in the cane sugar solution).

Incidentally, the non-destructive transmission optical measuring apparatus calibrator 5 according to the present embodiment has the form that the interiors of the linear cylindrical bodies 51 and 52 are filled with the cane sugar solution 6, but the interiors of the linear cylindrical bodies 51 and 52 need not necessarily be "filled" with the cane sugar solution 6. More specifically, on the upper sides of the linear cylindrical bodies 51 and 52, there may be an empty space or spaces where the cane sugar solution 6 is not present. However, since the presence of such an empty space(s) shortens, correspondingly thereto, the total light path length of the interiors of the linear cylindrical bodies 51 and 52 (the light path length at which the light travels through the interior of the cane sugar solution 6), the shortened portion ascribable to the empty space(s) must be taken into account when the geometrical lengths d of the linear cylindrical bodies 51 and 52 are set.

In the non-destructive transmission optical measuring apparatus calibrator 1 according to the first embodiment, too, the calibrator has the form that the interior of the linear cylindrical body 11 is filled with the cane sugar solution 2. In an instance where this non-destructive transmission optical measuring apparatus calibrator 1 is used in the sate it is set upright (i.e., in the state the light inlet 3 is on the topside and the light outlet 4 on the under side), there may be, on the upper side of the linear cylindrical body 11, an empty space where the cane sugar solution 2 is not present. In this instance, however, it follows that the surface of the cane sugar solution 2 in the linear cylindrical body 11 constitutes the light inlet 3 in the non-destructive transmission optical measuring apparatus calibrator 1, and the shortened portion ascribable to the empty space must be taken into account when the geometrical length d of the linear cylindrical body 11 is set.

On each of the inner wall surfaces of the pair of linear cylindrical bodies 51 and 52 from which surfaces the light having entered the calibrator 5 reflects and the inner wall surfaces of the member 54, a gold-plated light-reflecting film (not shown) is provided which has little dependence of reflectance on wavelength within the range of measuring light wavelengths and also has a good corrosion resistance.

In this calibrator 5, too, the light-transmitting member 55 of the linear cylindrical body 51, constituting the light inlet 7, and the light-transmitting member 58 of the linear cylindrical body 52, constituting the light outlet 8, are each fitted with a ready-made diffusion type attenuation plate and a ready-made aperture type attenuator in combination, the former having an equal attenuation for each measuring light having different wavelength. The amount of transmitted light is roughly adjusted by the diffusion type attenuation plate and also micro-adjusted by controlling the window diameter of the aperture type attenuator. Using these two types of attenuators, the amount of transmitted light of the calibrator is made equal to that of the measuring object.

The non-destructive transmission optical measuring apparatus calibrator according to the second embodiment constituted as described above is put in the preset measuring position in the non-destructive transmission optical measuring apparatus; the position being shown in FIG. 2A. Then, the light having entered the linear cylindrical body 51 from the light inlet 7 passes through the interior of the filled cane sugar solution 6 while repeating its reflection inside the linear cylindrical body 51, and comes into the cover member 54. Part of the light scattered and reflected in the cover member 54 enters the other linear cylindrical body 52, and the light having passed through the filled cane sugar solution 6 as in the linear cylindrical body 51 enters a detector (not shown) of the non-destructive transmission optical measuring apparatus from the light outlet 8. Thus, the sugar content of the cane sugar solution 6 with which the interior of the calibrator is filled can be determined like the fruit sugar content on the basis of the amount of light measured by the detector.

The difference in sugar content between the sugar content thus determined at the time of calibration and the reference sugar content of the cane sugar solution 6 in the calibrator which is previously measured under certain conditions is modulated by correcting it on a software of the non-destructive transmission optical measuring apparatus, thus the operation of calibration is completed. The fruit sugar content measured after the calibration can be an accurate sugar content from which any sugar content variations caused by the deviation in the measuring system in the non-destructive transmission optical measuring apparatus have been removed.

Figure 3:
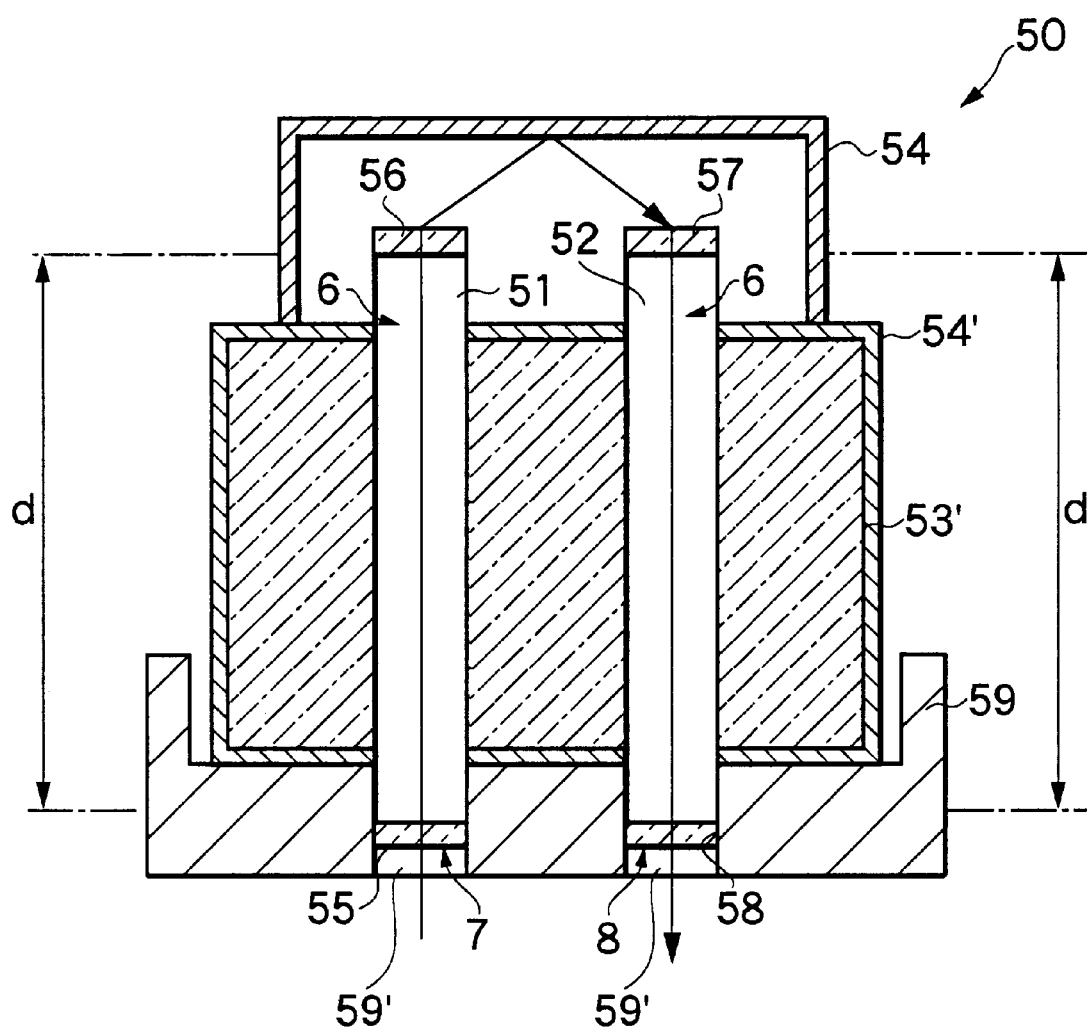
FIG. 3 is a schematic illustration showing a modification of the non-destructive transmission optical measuring apparatus calibrator according to the second embodiment.

FIG. 3 is a cross-sectional view of a non-destructive transmission optical measuring apparatus calibrator 50 which is a modification of the non-destructive transmission optical measuring apparatus calibrator 5 according to the second embodiment as shown in FIG. 2B.

More specifically, this non-destructive transmission optical measuring apparatus calibrator 50 is the same as the non-destructive transmission optical measuring apparatus calibrator according to the second embodiment as shown in FIG. 2B, except that the calibrator main body 53 formed of ABS (acrylonitrile-butadiene-styrene) resin is replaced with a calibrator main body 53' formed of a heat-insulating material such as foamed styrol, the calibrator main body 53' is covered on its periphery with a reinforcing cover 54' made of stainless steel, and also the linear cylindrical bodies 51 and 52 partly protrude outward from the calibrator main body 53' on the side of the light inlet 7 and light outlet 8.

When this non-destructive transmission optical measuring apparatus calibrator 50 is used, the calibrator 50 is used in the state it is received in a tray 59. More specifically, as shown in FIG. 3, the tray 59 has a pair of openings 59' and 59', and the non-destructive transmission optical measuring apparatus calibrator 50 is put into use in the state the linear cylindrical bodies 51 and 52 are fitted to the openings 59' and 59' of the tray on the side of the light inlet 7 and light outlet 8.

Third Embodiment

FIGS. 4A to 8C show a third embodiment of the present invention. The calibrator according to the present embodiment is a calibrator used for a non-destructive transmission optical measuring apparatus in which, as shown in FIG. 5C, a light-incident area 100 and a light-emergent area 200 with respect to a measuring object fruit (watermelon) M are positioned in the vicinity of the bottom of the fruit M.

Figure 4A:
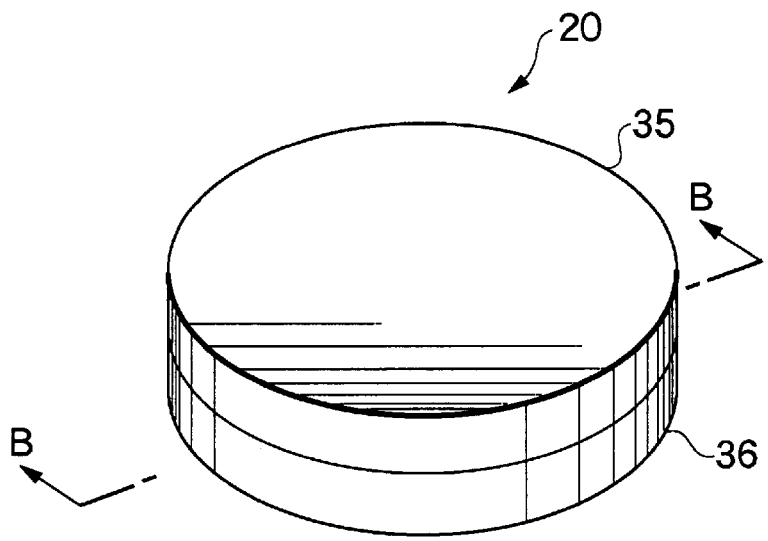
FIG. 4A is a schematic perspective view of a non-destructive transmission optical measuring apparatus calibrator according to a third embodiment of the present invention.
Figure 4B:
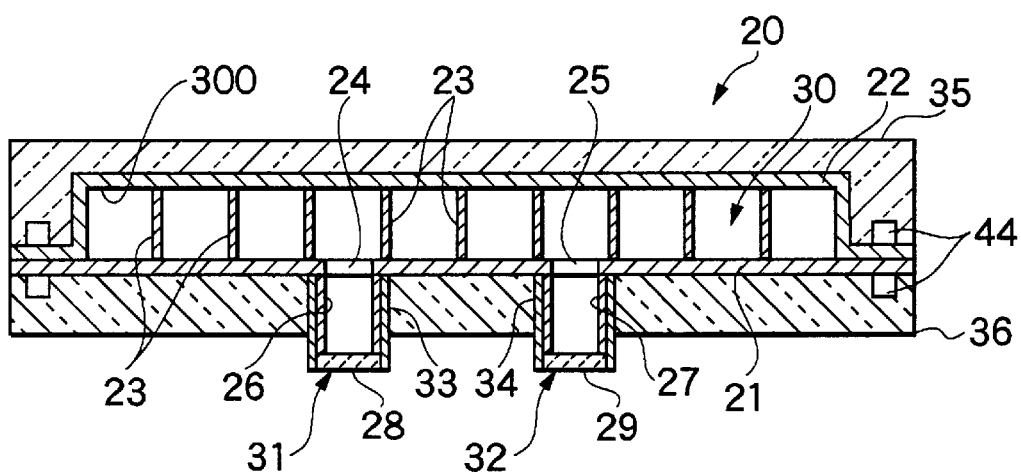
FIG. 4B is a cross-sectional view along the line B—B in FIG. 4A.

More specifically, as shown in FIGS. 4A and 4B, a non-destructive transmission optical measuring apparatus calibrator 20 according to the present embodiment is constituted chiefly of i) a circular, calibrator base disk 21 (see FIG. 6), ii) a packing-sealed cover 22 (see FIGS. 7A and 7B) which is attached to this calibrator base disk 21 and forms a closed body 300, iii) partitions 23 (see FIG. 6) made of stainless steel-which are fixed onto the calibrator base disk 21 and divide the interior of the closed body 300 into a plurality of spaces, iv) first and second openings 24 and 25 provided at substantially the center of the calibrator base disk 21, v) first and second inner cylindrical bodies 26 and 27 (see FIG. 7D) which are fixed on the back of the calibrator base disk 21 and in such a way that they communicate with the first and second openings 24 and 25, respectively, and also externally threaded, vi) first and second outer cylindrical bodies 33 and 34 (see FIG. 7E) which are fitted with light-transmitting members 28 and 29, respectively, on one open ends thereof and internally threaded, and also stand screwed onto the first and second inner cylindrical bodies 26 and 27 to form a light inlet 31 and a light outlet 32, respectively, and vii) a first heat-insulating member 35 fitted on the side of the cover 22 and a second insulating member 36 fitted on the side of the calibrator base disk 21. The interior of the closed body 300 is filled with a cane sugar solution 30 having a sugar content equal to that of the fruit (watermelon) M shown in FIG. 5C, and the plurality of spaces in the closed body 300 form a communicating path 40 (see FIG. 5A) which connects the light inlet 31 and the light outlet 32.

Figure 5A:
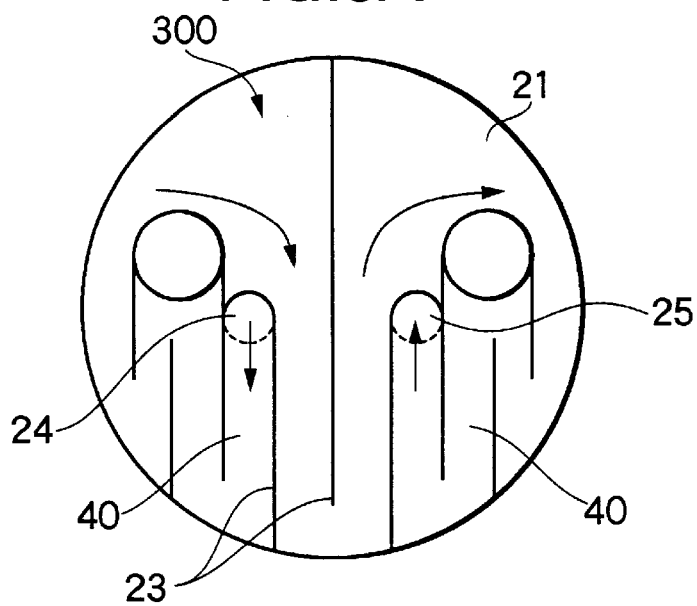
FIGS. 5A and 5B illustrate how the non-destructive transmission optical measuring apparatus calibrator according to the third embodiment operates.
Figure 5B:
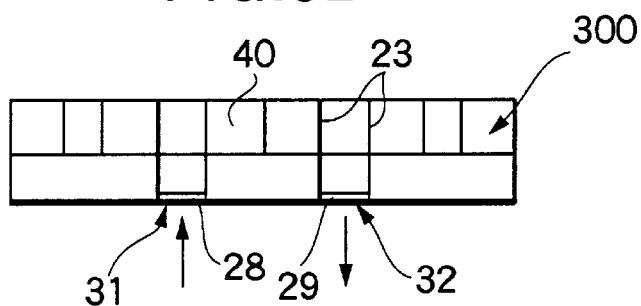
Figure 5C:
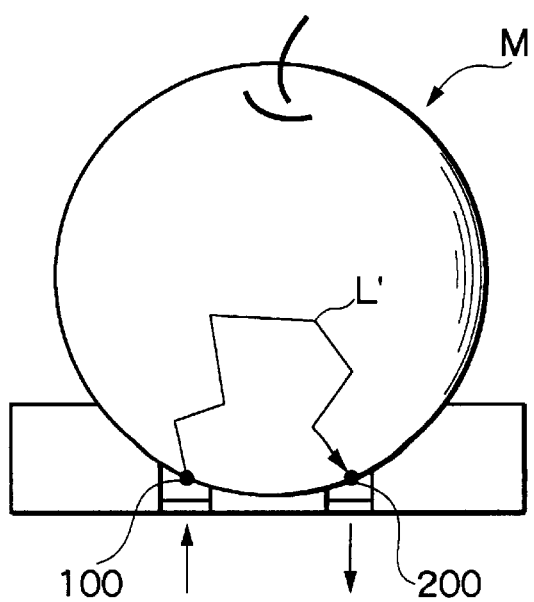
FIG. 5C is a schematic illustration of a non-destructive transmission optical measuring apparatus in which a light-incident area 100 and a light-emergent area 200 with respect to a fruit M are set in the vicinity of the bottom of the fruit.

The light path length from the light inlet 31 to the light outlet 32 of the calibrator 20 (i.e., the light path length of the interior of the closed body 300 filled with the cane sugar solution 30) is so set as to be substantially equal to the effective light path length L' of the light transmitted through the interior of the fruit (watermelon) M shown in FIG. 5C.

Here, the reason why the light path length from the light inlet 31 to the light outlet 32 of the calibrator 20 is adjusted to the effective light path length L' is the same as that in the calibrator 1 according to the first embodiment shown in FIG. 1.

Figure 18:
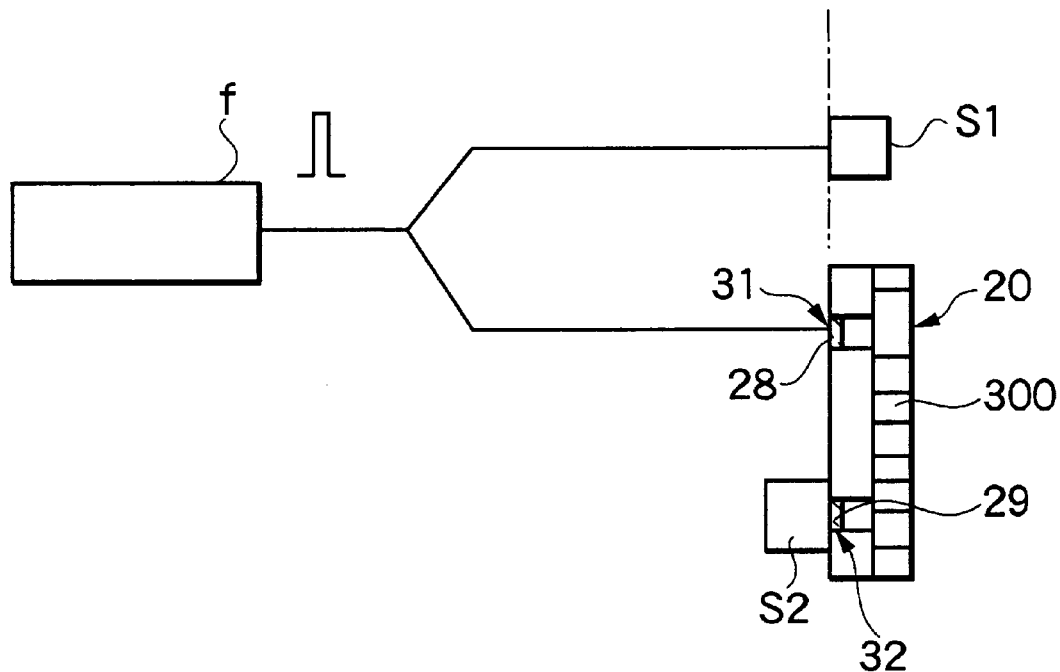
FIG. 18 illustrates an example of a measuring method for determining measured optical path length of the calibrator.
Figure 19:
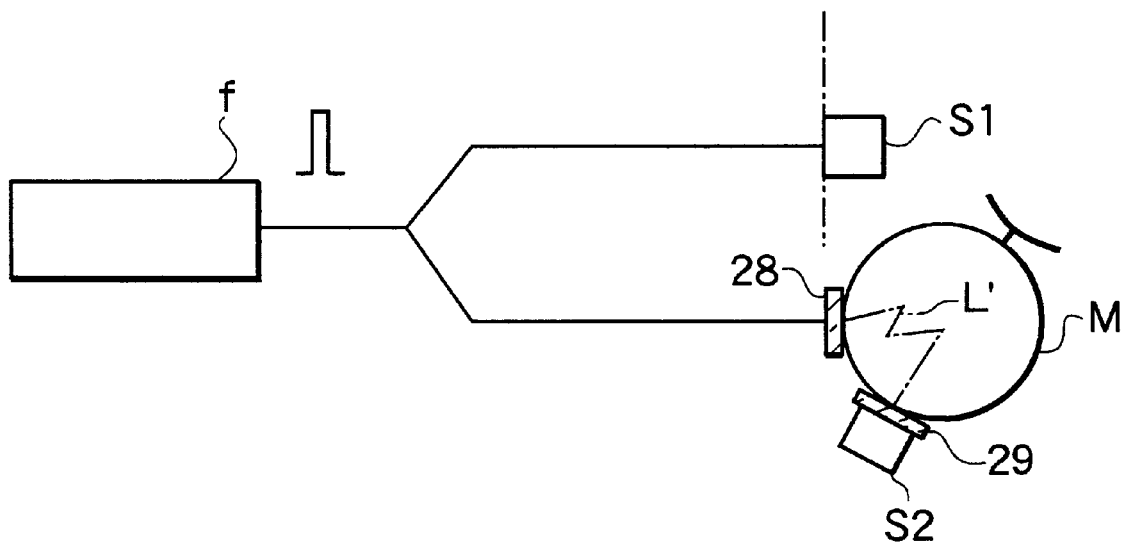
FIG. 19 illustrates an example of a measuring method for determining reference optical path length of a measuring object.

To set the light path length from the light inlet 31 to the light outlet 32 of the calibrator 20 substantially equal to the effective light path length L' of the light transmitted through the interior of the fruit (watermelon) M shown in FIG. 5C, first a measured optical path length of the calibrator 20 [i.e., optical path length obtained by adding i) a portion of optical path length given by the thickness of the light-transmitting members 28 and 29 and the thickness of the diffusion type attenuation plates, described later, attached to these light-transmitting members 28 and 29 to ii) the optical path length of the interior of the closed body 300 filled with the cane sugar solution 30] is determined by the following method as illustrated in FIG. 18, and then a reference optical path length obtained by adding i) a portion of optical path length given by the thickness of the light-transmitting members 28 and 29 and the thickness of the diffusion type attenuation plates, described later, attached to these light-transmitting members 28 and 29 to ii) the value obtained when the effective light path length L' is multiplied by n' (n' is a refractive index of the sarcocarp of the fruit M) is determined by the following method as illustrated in FIG. 19. Also, in an instance where the measured optical path length has a value smaller than the reference optical path length, the number of the partitions 23 is made larger to enlarge the length of the communicating path as long as necessary and, on the other hand, in an instance where the measured optical path length has a value larger than the reference optical path length, the number of the partitions 23 is made smaller or the disposition of the partitions 23 is changed to reduce the length of the communicating path as long as necessary so that the measured optical path length is adjusted to become substantially equal to the reference optical path length. Thus, the light path length from the light inlet 31 to the light outlet 32 of the calibrator 20 can be made substantially equal to the effective light path length L'.

More specifically, the measured optical path length of the calibrator 20 can be determined by, as shown in FIG. 18, using one pulse laser light source f and two detectors, first and second detectors S1 and S2. First, the distance from the pulse laser light source f to the first detector S1 is set equal to the distance from the pulse laser light source f to the light inlet 31 of the calibrator 20, and the pulse laser light emitted from the pulse laser light source f is branched at the middle of the light path. Also, the pulse laser light is made to enter the one first detector S1 directly and the pulse laser light transmitted through the interior of the closed body 300 of the calibrator 20 is made to enter the other second detector S2 disposed on the calibrator 20 in close contact with its light outlet 32. Then, the time difference Δt between pulses reaching the first and second detectors S1 and S2 is multiplied by light velocity C (C×Δt), thus the measured optical path length of the calibrator 20 can be determined.

The reference optical path length obtained by adding i) a portion of optical path length given by the thickness of the light-transmitting members 28 and 29 and the thickness of the diffusion type attenuation plates, described later, attached to these to ii) the value obtained when the effective light path length L' is multiplied by n' (n' is a refractive index of the sarcocarp of the fruit M) can be determined by, as shown in FIG. 19, using one pulse laser light source f and two detectors, first and second detectors S1 and S2, and also the light-transmitting members 28 and 29 and the diffusion type attenuation plates (not shown) attached thereto. First, the light-transmitting member 28 fitted with a diffusion type attenuation plate is disposed on the fruit M in close contact with its light-incident area, and the light-transmitting member 29 fitted with a diffusion type attenuation plate is disposed on the fruit M in close contact with its light-emergent area. Also, the second detector S2 is disposed on the light-transmitting member 29 in close contact with it. The distance from the pulse laser light source f to the first detector S1 is set equal to the distance from the pulse laser light source f to the light-transmitting member 28, and the pulse laser light emitted from the pulse laser light source f is branched at the middle of the light path. Also, the pulse laser light is made to enter the one first detector S1 directly and the pulse laser light transmitted through the interior of the fruit M is made to enter the other second detector S2. Then, the time difference Δt between pulses reaching the first and second detectors S1 and S2 is multiplied by light velocity C (C×Δt), thus the reference optical path length obtained by adding i) a portion of optical path length given by the thickness of the light-transmitting members 28 and 29 and the thickness of the diffusion type attenuation plates, described later, attached to these to ii) the value obtained when the effective light path length L' is multiplied by n' (n' is a refractive index of the sarcocarp of the fruit M) can be determined.

On each of the inner wall surfaces of the closed body 300 from which surfaces the measuring light having entered the calibrator 20 reflects (i.e., the surface of the calibrator base disk 21 and the inner wall surfaces of the cover 22) and the surfaces of the partitions 23, a gold-plated light-reflecting film (not shown) is provided which has little dependence of reflectance on wavelength within the range of measuring light wavelengths and also has a good corrosion resistance.

Incidentally, when the light-reflecting film forms a mirror face, the light having entered the closed body 300 from the light inlet 31 of the calibrator 20 may undergo specular reflection because of the light-reflecting film and part thereof may leak outside from the light inlet 31, so that the light having entered the closed body 300 may not travel smoothly through the interior of the communicating path. In such a case, the inner wall surfaces of the closed body 300 may be roughed so that the light-reflecting film can function as a diffusible reflecting film. When, however, a diffusion plate (diffusion type attenuation plate) described later is provided on the side of the light inlet 31, the light thus diffused enters the closed body 300, and hence the light having entered it can be prevented from leaking without the surface-roughing.

In this calibrator 20, too, the light-transmitting members 28 and 29 at the light inlet 31 and light outlet 32 are each fitted with a ready-made diffusion type attenuation plate and a ready-made aperture type attenuator in combination, the former having an equal attenuation for each measuring light having different wavelength. The amount of transmitted light is roughly adjusted by the diffusion type attenuation plate and also micro-adjusted by controlling the window diameter of the aperture type attenuator. Using these two types of attenuators, the amount of transmitted light of the calibrator is made equal to that of the measuring object.

Figure 4C:
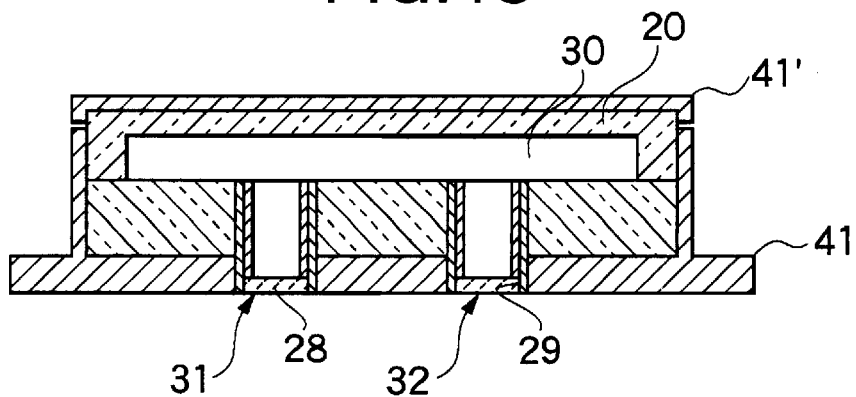
FIG. 4C shows how the non-destructive transmission optical measuring apparatus calibrator according to the third embodiment is used.

The non-destructive transmission optical measuring apparatus calibrator 20 according to the third embodiment constituted as described above is placed on a tray 41 as shown in FIG. 4C and put in the preset measuring position in the non-destructive transmission optical measuring apparatus. Then, as shown in FIGS. 5A and 5B, the light having entered the closed body 300 from the light inlet 31 passes through the interior of the filled cane sugar solution 30 while repeating its reflection inside the closed body 300 divided by the partitions 23 into a plurality of spaces, and enters a detector (not shown) of the non-destructive transmission optical measuring apparatus from the light outlet 32. Thus, the sugar content of the cane sugar solution 30 with which the interior of the calibrator is filled can be determined like the fruit sugar content on the basis of the amount of light measured by the detector. In FIG. 4C, reference numeral 41' denotes a tray cover.

The difference in sugar content between the sugar content thus determined at the time of calibration and the reference sugar content of the cane sugar solution 30 in the calibrator which is previously measured under certain conditions is modulated by correcting it on a software of the non-destructive transmission optical measuring apparatus, thus the operation of calibration is completed. The fruit sugar content measured after the calibration can be an accurate sugar content from which any sugar content variations caused by the deviation in the measuring system in the non-destructive transmission optical measuring apparatus have been removed.

The non-destructive transmission optical measuring apparatus calibrator 20 according to the present embodiment is assembled in the following way.

FIG. 6 shows the calibrator base disk 21 having the first opening 24 and second opening 25 and the partitions 23 fixed onto this base disk 21.

First, grid-pattern bolts 42 are provided vertically on the surface of the calibrator base disk 21, and these grid-pattern bolts 42 are fitted to fixing holes provided on the base ends of the partitions 23, and are fastened with nuts 43. As the partitions 23, those of types having different shapes are prepared, including L-shaped partitions 231 fixed vertically to the surface of the calibrator base disk 21, L-shaped partitions 232 having a curved surface partly, and square partitions 233 having an inclination with respect to the surface of the calibrator base disk 21 and fixed thereto in the vicinity of the first opening 24, and second opening 25 so that the light can effectively be cast to and fro inside and outside the calibrator. Then, considering the preset light path length in the calibrator, these partitions 23 are appropriately fixed to the surface of the calibrator base disk 21 as shown in FIG. 7C.

Figure 8A:
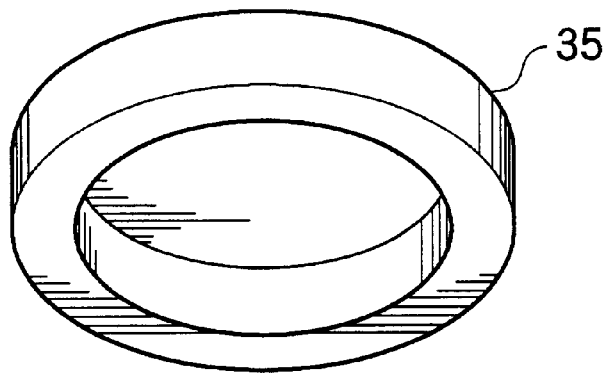
FIG. 8A is a bottom perspective view of a first insulating member which constitutes part of the non-destructive transmission optical measuring apparatus calibrator according to the third embodiment.
Figure 8B:
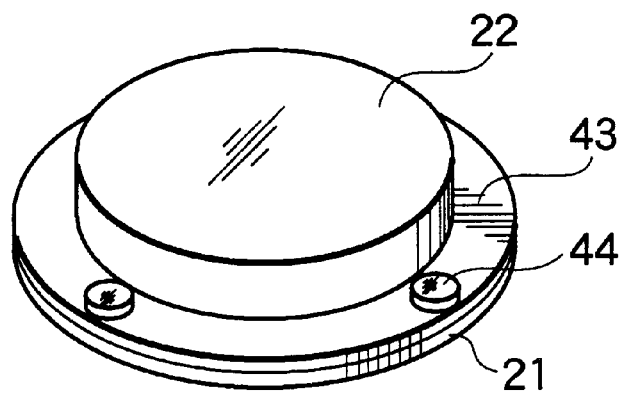
FIG. 8B is a top perspective view of the calibrator base disk and cover in the course of their assemblage, which constitute part of the non-destructive transmission optical measuring apparatus calibrator according to the third embodiment.

Then, to the calibrator base disk 21 to which the partitions 23 have been fixed, a cover 22 made of stainless steel, having the shape of a hat as shown in FIGS. 7A and 7B and having a packing (not shown) is attached on its surface side, and also a flange 43 of the cover 22 and the peripheral edge of the calibrator base disk 21 are fastened with an appropriate fastening means 44 constituted of bolts and nuts as shown in FIG. 8B.

Next, the cane sugar solution is put into the closed body 300 through at least one of the first and second inner cylindrical bodies 26 and 27 fixed to the back of the calibrator main body integrally formed of the calibrator base disk 21 and the cover 22, i.e., to the back of the calibrator base disk 21. Also, as shown in FIGS. 7D to 7E, the first and second outer cylindrical bodies 33 and 34 are screwed onto the first and second inner cylindrical bodies 26 and 27 to form the light inlet 31 and light outlet 32, respectively.

Figure 8C:
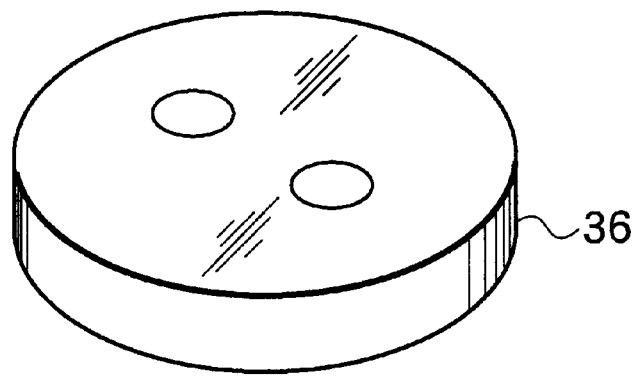
FIG. 8C is a top perspective view of a second insulating member which constitutes part of the non-destructive transmission optical measuring apparatus calibrator according to the third embodiment.

Then, as shown in FIGS. 8A to 8C, a first heat-insulating member 35 constituted of foamed styrol is fitted to the calibrator main body integrally formed of the calibrator base disk 21 and the cover 22; the former being fitted on the surface side of the latter. Also, a second insulating member 36 similarly constituted of foamed styrol is fitted thereto on the back side of the calibrator main body. Thus, the non-destructive transmission optical measuring apparatus calibrator 20 according to the third embodiment is assembled.

In this non-destructive transmission optical measuring apparatus calibrator 20, the calibrator may be made to have a structure wherein the outer surfaces of the first and second heat-insulating member 35 and 36 are covered with a reinforcing cover made of stainless steel.

Fourth Embodiment

FIGS. 9A to 9C show a fourth embodiment of the present invention. The calibrator according to the present embodiment is a calibrator used for a non-destructive transmission optical measuring apparatus in which, as shown in FIG. 9C, a light-incident area 100 and a light-emergent area 200 with respect to a measuring object fruit (watermelon) M are positioned in the vicinity of the equator of the fruit M.

More specifically, as shown in FIGS. 9A and 9B, a non-destructive transmission optical measuring apparatus calibrator 60 according to the present embodiment is constituted chiefly of i) a closed body 63 having the shape of a rectanglar parallelopiped and provided with a light inlet 61 and a light outlet 62 on its upper side, ii) light-transmitting members 64 and 65 fixed to the light inlet 61 and light outlet 62, respectively, and iii) partitions 66 which are fixed inside the closed body 63 and divide the interior of the closed body 63 into a plurality of spaces. Also, the interior of the closed body 63 is filled with a cane sugar solution 67 having a sugar content equal to that of the fruit (watermelon) M shown in FIG. 9C, and the plurality of spaces in the closed body 63 form a communicating path 68 which connects the light inlet 61 and the light outlet 62.

The light path length from the light inlet 61 to the light outlet 62 of the calibrator 60 (i.e., the light path length of the interior of the closed body 63 filled with the cane sugar solution 67) is so set as to be substantially equal to the effective light path length L' of the light transmitted through the interior of the fruit (watermelon) M shown in FIG. 9C.

Here, the reason why the light path length from the light inlet 61 to the light outlet 62 of the calibrator 60 is adjusted to the effective light path length L' is the same as that in the calibrator 1 according to the first embodiment shown in FIG. 1.

To set the light path length from the light inlet 61 to the light outlet 62 of the calibrator 60 substantially equal to the effective light path length L' of the light transmitted through the interior of the fruit (watermelon) M shown in FIG. 9C, first a measured optical path length of the calibrator 60 [i.e., optical path length obtained by adding i) a portion of optical path length given by the thickness of the light-transmitting members 64 and 65 and the thickness of the diffusion type attenuation plates, described later, attached to these light-transmitting members 64 and 65 to ii) the optical path length of the interior of the closed body 63 filled with the cane sugar solution 67] is determined by the above method as illustrated in FIG. 18, and then a reference optical path length obtained by adding i) a portion of optical path length given by the thickness of the light-transmitting members 64 and 65 and the thickness of the diffusion type attenuation plates, described later, attached to these light-transmitting members 64 and 65 to ii) the value obtained when the effective light path length L' is multiplied by n' (n' is a refractive index of the sarcocarp of the fruit M) is determined by the above method as illustrated in FIG. 19. Also, in an instance where the measured optical path length has a value smaller than the reference optical path length, the number of the partitions 66 is made larger to enlarge the length of the communicating path as long as necessary and, on the other hand, in an instance where the measured optical path length has a value larger than the reference optical path length, the number of the partitions 66 is made smaller or the disposition of the partitions 66 is changed to reduce the length of the communicating path as long as necessary so that the measured optical path length is adjusted to become substantially equal to the reference optical path length. Thus, the light path length from the light inlet 61 to the light outlet 62 of the calibrator 60 can be made substantially equal to the effective light path length L'.

On each of the inner wall surfaces of the closed body 63 from which surfaces the measuring light having entered the calibrator 60 reflects and the surfaces of the partitions 66, a gold-plated light-reflecting film (not shown) is provided which has little dependence of reflectance on wavelength within the range of measuring light wavelengths and also has a good corrosion resistance.

In this calibrator 60, too, the light-transmitting members 64 and 65 at the light inlet 61 and light outlet 62 are each fitted with a ready-made diffusion type attenuation plate and a ready-made aperture type attenuator in combination, the former having an equal attenuation for each measuring light having different wavelength. The amount of transmitted light is roughly adjusted by the diffusion type attenuation plate and also micro-adjusted by controlling the window diameter of the aperture type attenuator. Using these two types of attenuators, the amount of transmitted light of the calibrator is made equal to that of the measuring object.

The non-destructive transmission optical measuring apparatus calibrator 60 according to the fourth embodiment constituted as described above is put in the preset measuring position in the non-destructive transmission optical measuring apparatus. Then, as shown in FIGS. 9A and 9B, the light having entered the closed body 63 from the light inlet 61 passes through the interior of the filled cane sugar solution 67 while repeating its reflection and making turns inside the closed body 63 divided by the partitions 66 into a plurality of spaces, and enters a detector (not shown) of the non-destructive transmission optical measuring apparatus from the light outlet 62. Thus, the sugar content of the cane sugar solution 67 with which the interior of the calibrator is filled can be determined like the fruit sugar content on the basis of the amount of light measured by the detector.

The difference in sugar content between the sugar content thus determined at the time of calibration and the reference sugar content of the cane sugar solution 67 in the calibrator which is previously measured under certain conditions is modulated by correcting it on a software of the non-destructive transmission optical measuring apparatus, thus the operation of calibration is completed. The fruit sugar content measured after the calibration can be an accurate sugar content from which any sugar content variations caused by the deviation in the measuring system in the non-destructive transmission optical measuring apparatus have been removed.

Fifth Embodiment

Figure 10A:
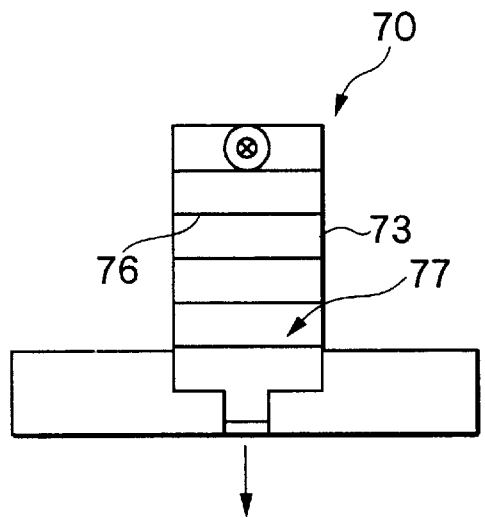
FIG. 10A is a sectional front elevation of a non-destructive transmission optical measuring apparatus calibrator according to a fifth embodiment of the present invention.
Figure 10B:
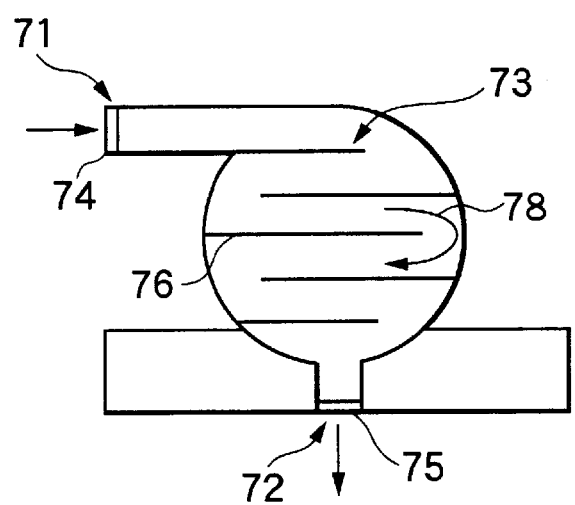
FIG. 10B is a sectional side elevation thereof.
Figure 10C:
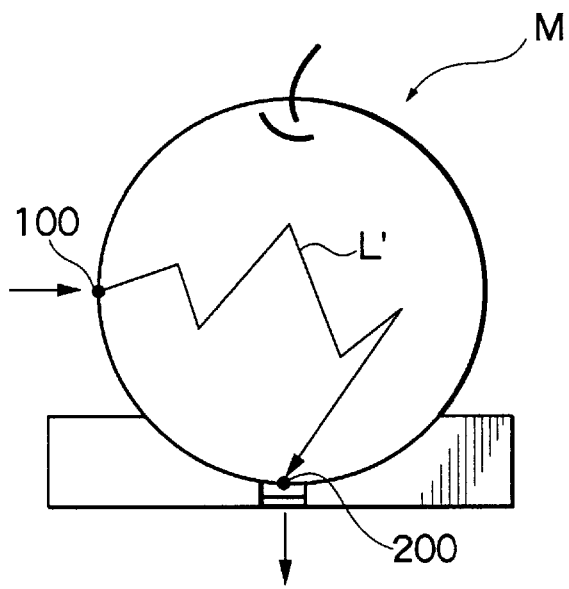
FIG. 10C is a schematic illustration of a non-destructive transmission optical measuring apparatus in which a light-incident area 100 and a light-emergent area 200 with respect to a fruit M are set in the vicinity of the equator of the fruit and in the vicinity of the bottom of the fruit, respectively.

FIGS. 10A to 10C show a fifth embodiment of the present invention. The calibrator according to the present embodiment is a calibrator used for a non-destructive transmission optical measuring apparatus in which, as shown in FIG. 10C, a light-incident area 100 and a light-emergent area 200 with respect to a measuring object fruit (watermelon) M are positioned in the vicinity of the equator of the fruit M and in the vicinity of the bottom of the fruit M, respectively.

More specifically, as shown in FIGS. 10A and 10B, a non-destructive transmission optical measuring apparatus calibrator 70 according to the present embodiment is constituted chiefly of i) a closed body 73 having substantially the shape of a cylinder and provided with a light inlet 71 and a light outlet 72 on its upper side and lower side, respectively, ii) light-transmitting members 74 and 75 fixed to the light inlet 71 and light outlet 72, respectively, and iii) partitions 76 which are fixed inside the closed body 73 and divide the interior of the closed body 73 into a plurality of spaces. Also, the interior of the closed body 73 is filled with a cane sugar solution 77 having a sugar content equal to that of the fruit (watermelon) M shown in FIG. 10C, and the plurality of spaces in the closed body 73 form a communicating path 78 which connects the light inlet 71 and the light outlet 72.

The light path length from the light inlet 71 to the light outlet 72 of the calibrator 70 (i.e., the light path length of the interior of the closed body 73 filled with the cane sugar solution 77) is so set as to be substantially equal to the effective light path length L' of the light transmitted through the interior of the fruit (watermelon) M shown in FIG. 10C.

Here, the reason why the light path length from the light inlet 71 to the light outlet 72 of the calibrator 70 is adjusted to the effective light path length L' is the same as that in the calibrator 1 according to the first embodiment shown in FIG. 1.

To set the light path length from the light inlet 71 to the light outlet 72 of the calibrator 70 substantially equal to the effective light path length L' of the light transmitted through the interior of the fruit (watermelon) M shown in FIG. 10C, first a measured optical path length of the calibrator 70 [i.e., optical path length obtained by adding i) a portion of optical path length given by the thickness of the light-transmitting members 74 and 75 and the thickness of the diffusion type attenuation plates, described later, attached to these light-transmitting members 74 and 75 to ii) the optical path length of the interior of the closed body 73 filled with the cane sugar solution 77] is determined by the above method as illustrated in FIG. 18, and then a reference optical path length obtained by adding i) a portion of optical path length given by the thickness of the light-transmitting members 74 and 75 and the thickness of the diffusion type attenuation plates, described later, attached to these light-transmitting members 74 and 75 to ii) the value obtained when the effective light path length L' is multiplied by n' (n' is a refractive index of the sarcocarp of the fruit M) is determined by the above method as illustrated in FIG. 19. Also, in an instance where the measured optical path length has a value smaller than the reference optical path length, the number of the partitions 76 is made larger to enlarge the length of the communicating path as long as necessary and, on the other hand, in an instance where the measured optical path length has a value larger than the reference optical path length, the number of the partitions 76 is made smaller or the disposition of the partitions 76 is changed to reduce the length of the communicating path as long as necessary so that the measured optical path length is adjusted to become substantially equal to the reference optical path length. Thus, the light path length from the light inlet 71 to the light outlet 72 of the calibrator 70 can be made substantially equal to the effective light path length L'.

On each of the inner wall surfaces of the closed body 73 from which surfaces the measuring light having entered the calibrator 70 reflects and the surfaces of the partitions 76, a gold-plated light-reflecting film (not shown) is provided which has little dependence of reflectance on wavelength within the range of measuring light wavelengths and also has a good corrosion resistance.

In this calibrator 70, too, the light-transmitting members 74 and 75 at the light inlet 71 and light outlet 72 are each fitted with a ready-made diffusion type attenuation plate and a ready-made aperture type attenuator in combination, the former having an equal attenuation for each measuring light having different wavelength. The amount of transmitted light is roughly adjusted by the diffusion type attenuation plate and also micro-adjusted by controlling the window diameter of the aperture type attenuator. Using these two types of attenuators, the amount of transmitted light of the calibrator is made equal to that of the measuring object.

The non-destructive transmission optical measuring apparatus calibrator 70 according to the fifth embodiment constituted as described above is put in the preset measuring position in the non-destructive transmission optical measuring apparatus. Then, as shown in FIGS. 10A and 10B, the light having entered the closed body 73 from the light inlet 71 passes through the interior of the filled cane sugar solution 77 while repeating its reflection and making turns inside the closed body 73 divided by the partitions 76 into a plurality of spaces, and enters a detector (not shown) of the non-destructive transmission optical measuring apparatus from the light outlet 72. Thus, the sugar content of the cane sugar solution 77 with which the interior of the calibrator is filled can be determined like the fruit sugar content on the basis of the amount of light measured by the detector.

The difference in sugar content between the sugar content thus determined at the time of calibration and the reference sugar content of the cane sugar solution 77 in the calibrator which is previously measured under certain conditions is modulated by correcting it on a software of the non-destructive transmission optical measuring apparatus, thus the operation of calibration is completed. The fruit sugar content measured after the calibration can be an accurate sugar content from which any sugar content variations caused by the deviation in the measuring system in the non-destructive transmission optical measuring apparatus have been removed.

EXAMPLES

Example 1

A specific manner for the calibrator shown in FIG. 2B intended for muskmelons as measuring objects will be described below.

A cane sugar solution having a sugar content of 13% corresponding to the sugar content of muskmelons on the average was used as the aqueous solution with which the linear cylindrical bodies 51 and 52 in the calibrator 5 were filled. On each of the inner wall surfaces of the linear cylindrical bodies and the inner wall surfaces of the cover member 54, a gold-plated light-reflecting film (not shown) was provided. A diffusion type attenuation plate containing CaF was directly used as each of the light-transmitting member 55 of the linear cylindrical body 51, constituting the light inlet 7, and the light-transmitting member 58 of the linear cylindrical body 52, constituting the light outlet 8. Transparent glass was used as the light-transmitting members 56 and 57.

In addition to each CaF attenuation plate, an aperture type attenuator of 1 cm diameter was also attached to make the amount of transmitted light of the calibrator substantially equal to that of the muskmelon. Here, the two linear cylindrical bodies 51 and 52 each had an inner diameter of 2 cm.

The light-incident and light-emergent openings (windows) corresponding to the light-incident and light-emergent areas 100 and 200, of the non-destructive transmission optical measuring apparatus were positioned at the bottom of the fruit (muskmelon) M as shown in FIG. 2A. In the muskmelon situated in this way, the value obtained when its average effective light path length was multiplied by refractive index n' of the sarcocarp was 48 cm as measured using the pulse laser described previously (see FIG. 17).

Next, with regard to the 2 cm diameter linear cylindrical bodies filled with the cane sugar solution having a sugar content of 13%, the value obtained when their light path length ΔL" per 1 cm of cylinder length was multiplied by refractive index n" of the cane sugar solution was actually measured by the method described previously (see FIG. 16) to find that it was 1.4 cm.

Accordingly, the value of 48 (cm) obtained when the average effective light path length was multiplied by refractive index n' of the sarcocarp was equally shared to the two linear cylindrical bodies 51 and 52. More specifically, the geometrical length d of the light-inlet side and light-outlet side linear cylindrical bodies 51 and 52 each was set at 48÷1.4÷2=17 (cm), thus the effective light path length of the calibrator was adjusted to the average effective light path length of the muskmelon.

Figure 11:
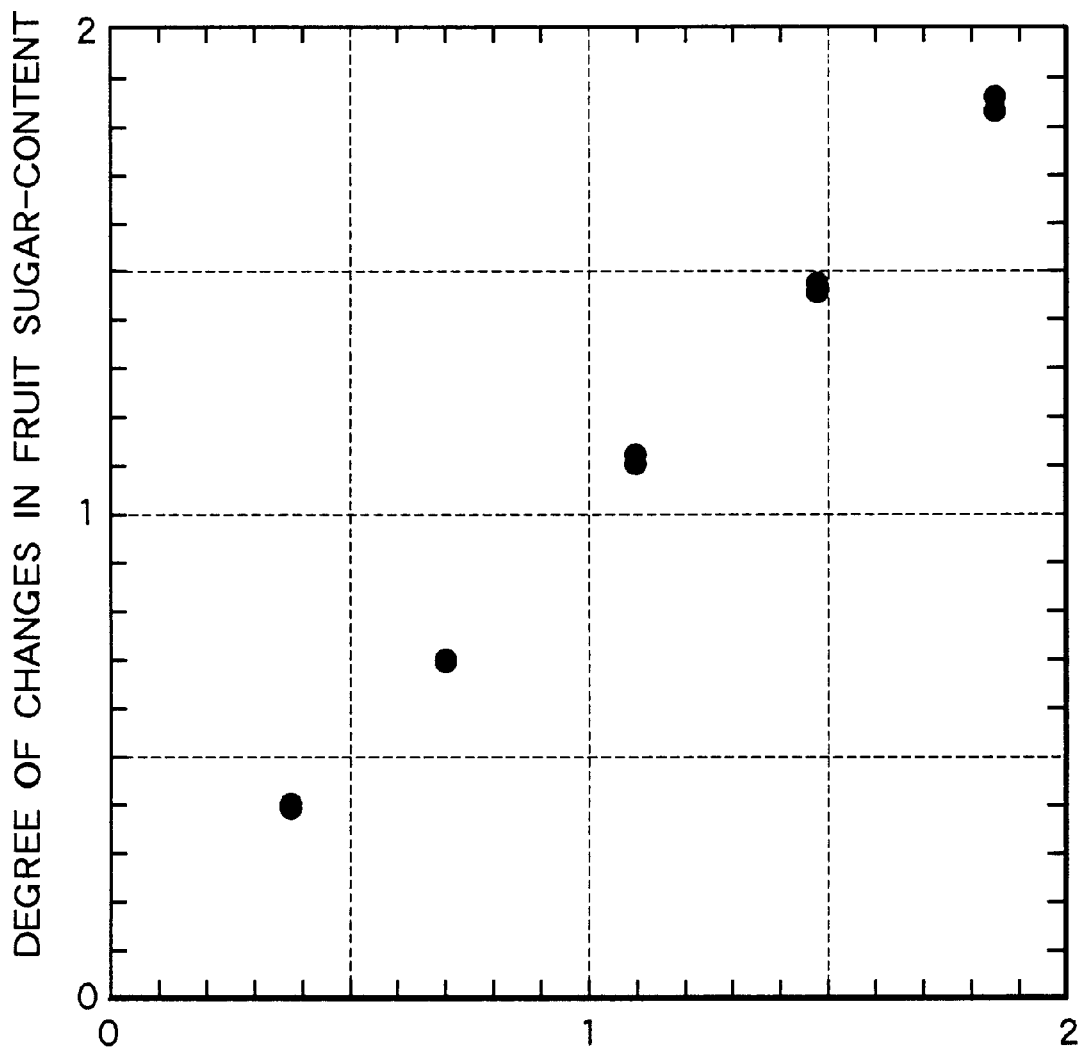
FIG. 11 is a graph showing changes in sugar content which are caused by changes in the amount of transmitted light.

Using such a calibrator, variations of sugar content of actual muskmelons with respect to calibrator sugar content were measured under various variational conditions intentionally produced according to what was imaginable in non-destructive measurement. Temperatures of the calibrator and muskmelons were previously set to equal temperature. Dust was put to the light-incident and light-emergent windows of the non-destructive transmission optical measuring apparatus to cause the amount of transmitted light to attenuate intentionally, where the degree of changes in actual-muskmelon sugar content with respect to the degree of changes in calibrator sugar content was plotted as shown in FIG. 11. The measuring light wavelength of the non-destructive transmission optical measuring apparatus was also made to deviate intentionally, where the degree of changes in actual-muskmelon sugar content with respect to the degree of changes in calibrator sugar content was plotted as shown in FIG. 12.

Figure 12:
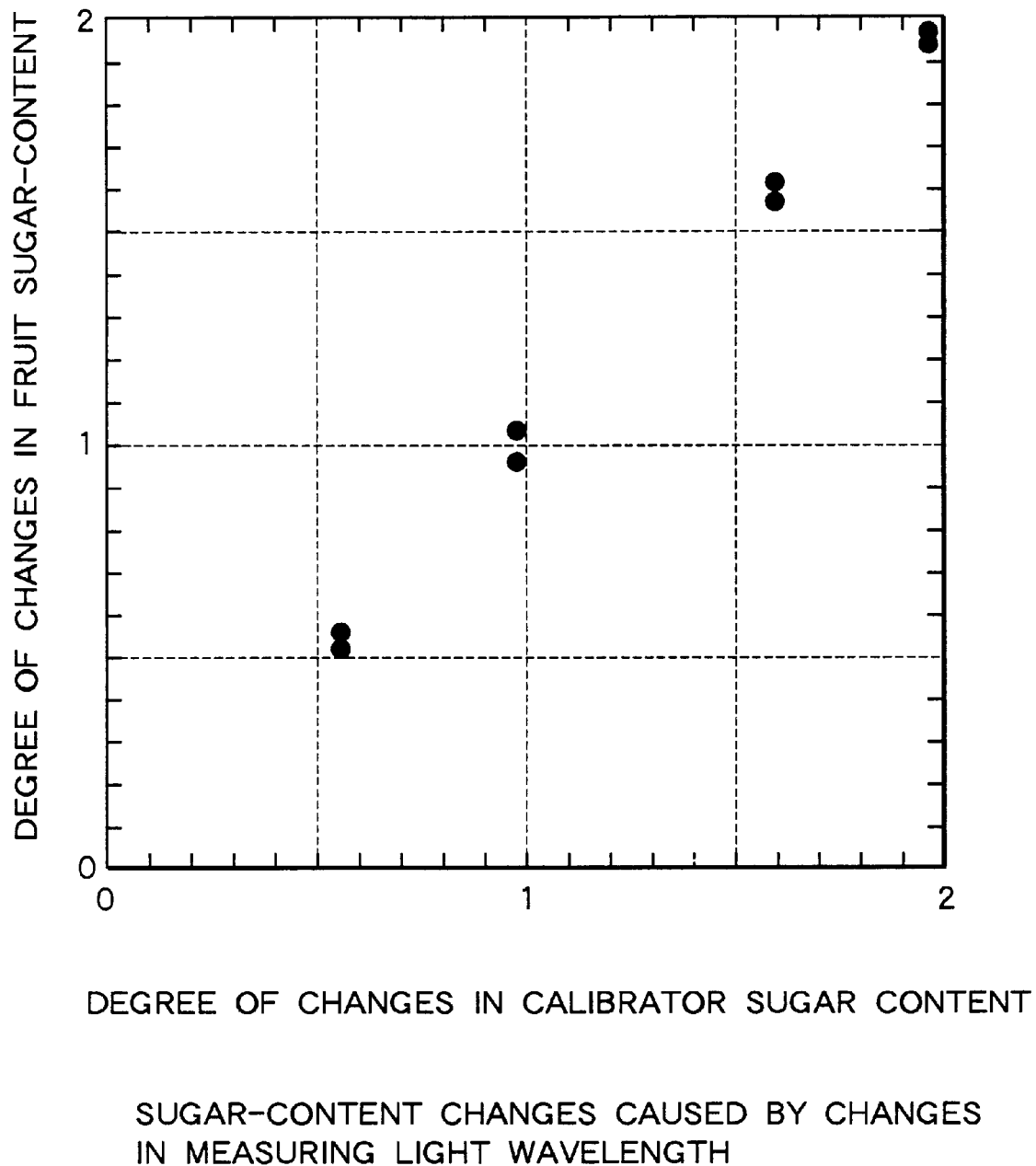
FIG. 12 is a graph showing changes in sugar content which are caused by changes in measuring light wavelength.

As can be seen from the graphs in FIGS. 11 and 12, the changes in sugar content proved to be substantially identical between the calibrator and the actual muskmelons even when the amount of transmitted light changed or the measuring light wavelength changed.

Figure 13:
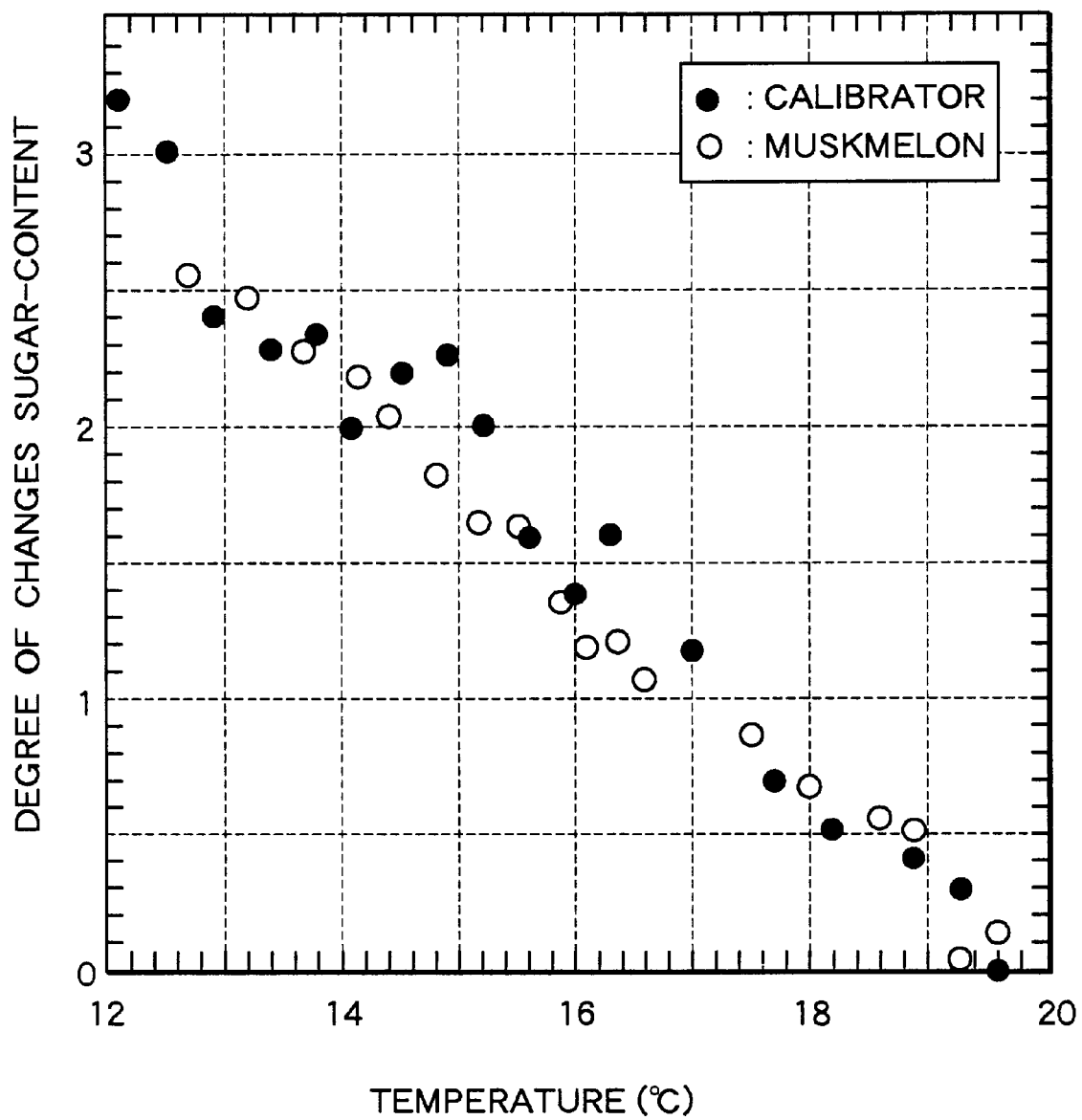
FIG. 13 is a graph showing changes in sugar content which are caused by changes in temperature.
Figure 14:
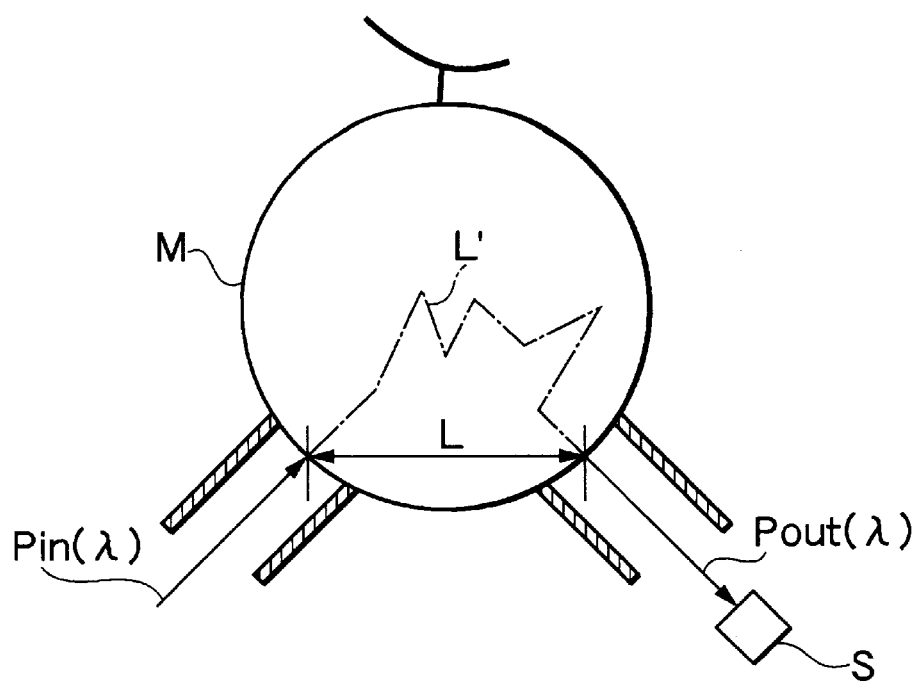
FIG. 14 illustrates how a non-destructive transmission optical measuring apparatus operates.

Changes in sugar content in an instance where the calibrator and actual muskmelons changed in temperature are also shown in FIG. 13. As can be seen from the graph in FIG. 13, the degree of changes in sugar content caused by the changes in temperature proved to be substantially identical between the calibrator and the actual muskmelons.

Example 2

A specific manner for the calibrator shown in FIGS. 4A and 4B intended for watermelons as measuring objects will be described below.

A cane sugar solution having a sugar content of 10% corresponding to the sugar content of watermelons on the average was used as the aqueous solution with which the closed body 300 of the calibrator was filled. On each of the inner wall surfaces of the closed body 300 and the surfaces of the partitions 23, a gold-plated light-reflecting film (not shown) was provided. A 1.5 mm thick ,diffusion type attenuation plate containing CaF was directly used as each of the light-transmitting members 28 and 29 of the light inlet 31 and the light outlet 32, respectively. In addition to each CaF attenuation plate, an aperture type attenuator of 1 cm diameter was also attached to make the amount of transmitted light of the calibrator substantially equal to that of the watermelon.

The partitions 23 were appropriately disposed so that the light path length of the closed body 300 filled with the cane sugar solution having a sugar content of 10% came to be substantially equal to the average effective light path length of the watermelon, thus the calibrator shown in FIGS. 4A and 4B was assembled.

The light path length of the closed body 300 was made substantially equal to the average effective light path length of the watermelon by the methods illustrated in FIGS. 18 and 19.

More specifically, the measured optical path length of the closed body 300 was first determined by the method illustrated in FIGS. 18, and the reference optical path length obtained by adding i) a portion of optical path length given by the thickness of the diffusion type attenuation plates to ii) the value obtained when the effective light path length L' is multiplied by n' (n' is a refractive index of the sarcocarp of the watermelon) was determined by the method illustrated in FIG. 19. Also, in an instance where the measured optical path length had a value smaller than the reference optical path length, the number of the partitions was made larger to enlarge the length of the communicating path as long as necessary and, on the other hand, in an instance where the measured optical path length had a value larger than the reference optical path length, the number of the partitions was made smaller or the disposition of the partitions was changed to reduce the length of the communicating path as long as necessary so that the measured optical path length was adjusted to become substantially equal to the reference optical path length. Thus, the light path length of the closed body 300 was made substantially equal to the average effective light path length.

Using such a calibrator, variations of sugar content of actual watermelons with respect to calibrator sugar content were measured under various variational conditions intentionally produced according to what was imaginable in non-destructive measurement. Temperatures of the calibrator and watermelons were previously set to equal temperature. Dust was put to the light-incident and light-emergent windows of the non-destructive transmission optical measuring apparatus to cause the amount of transmitted light to attenuate intentionally, where the degree of changes in actual-watermelon sugar content with respect to the degree of changes in calibrator sugar content showed the same tendency as the case of actual muskmelons (see FIG. 11). The measuring light wavelength of the non-destructive transmission optical measuring apparatus was also made to deviate intentionally, where the degree of changes in actual-watermelon sugar content with respect to the degree of changes in calibrator sugar content showed the same tendency as the case of actual muskmelons (see FIG. 12). From these facts, it was confirmed that the changes in sugar content were substantially identical between the calibrator and the actual watermelons even when the amount of transmitted light changed or the measuring light wavelength changed.

Changes in sugar content in an instance where the calibrator and actual watermelons changed in temperature also showed the same tendency as the case of actual muskmelons (see FIG. 13), and it was confirmed that the degree of changes in sugar content caused by the changes in temperature was substantially identical between the calibrator and the actual watermelons.

What is claimed is:

1. A calibrator used for a non-destructive transmission optical measuring apparatus for quantitatively determining a specific component contained in a measuring object by making light incident on the measuring object at its light-incident area, detecting the light having entered, and having been transmitted through, an interior of the measuring object, at its light-emergent area set at a position different from the light-incident area, and measuring absorption of the light to quantitatively determine the specific component contained in the measuring object; the calibrator comprising;

a closed body having a light inlet and a light outlet, an interior of which is provided with a substance having light absorption characteristics identical or similar to those of the specific component, and in which a light path length from the light inlet to the light outlet is so set as to be equal or substantially equal to an effective light path length of the light transmitted through the interior of the measuring object.

2. The calibrator according to claim 1, wherein said closed body comprises;

a pair of linear cylindrical bodies having inner wall surfaces having light-reflecting properties, interiors of which are provided with said substance and open ends of which are each closed with a light transmitting member; and a cover member so provided as to cover one ends of the linear cylindrical bodies, having inner wall surfaces having light-reflecting properties, and by which the light emergent from an end of one linear cylindrical body is made incident on an end of the other linear cylindrical body; the other ends of the linear cylindrical bodies constituting the light inlet and light outlet of the closed body.

3. The calibrator according to claim 1, wherein the interior of said closed body is divided by partitions into a plurality of spaces, the spaces form a communicating path which connects the light inlet and the light outlet, and the wall surfaces of the communicating path have light-reflecting properties.

4. The calibrator according to claim 3, wherein said partitions comprise a detachable member so that the length of the communicating path is adjustable by at least one of attaching and detaching the partitions.

5. The calibrator according to any one of claims 1 to 4, wherein a light attenuator is provided at each of the light inlet and the light outlet.

6. The calibrator according to claim 5, wherein the attenuation attributable to the light attenuator is equal or substantially equal for each measuring light having different wavelength.

7. The calibrator according to claim 5, wherein said light attenuator has light-diffusion properties.

8. The calibrator according to claim 5, wherein the interior of said closed body has a light-scattering material together with the substance having light absorption characteristics identical or similar to those of the specific component.

* * * * *